United States Patent
Tanabe

(10) Patent No.: US 8,107,063 B2
(45) Date of Patent: Jan. 31, 2012

(54) TRANSPARENT ARTICLE

(75) Inventor: Masaru Tanabe, Tokyo (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 12/974,400

(22) Filed: Dec. 21, 2010

(65) Prior Publication Data

US 2011/0097652 A1    Apr. 28, 2011

Related U.S. Application Data

(62) Division of application No. 11/816,617, filed as application No. PCT/JP2006/302612 on Feb. 15, 2006, now Pat. No. 7,898,650.

(30) Foreign Application Priority Data

| | | |
|---|---|---|
| Feb. 18, 2005 | (JP) | 2005-043134 |
| Aug. 5, 2005 | (JP) | 2005-228598 |
| Aug. 25, 2005 | (JP) | 2005-244044 |

(51) Int. Cl.
*G01N 21/00* (2006.01)

(52) U.S. Cl. ............................ 356/237.1; 356/237.2

(58) Field of Classification Search ..... 356/237.1–237.5
See application file for complete search history.

(56) References Cited

U.S. PATENT DOCUMENTS

| | | | |
|---|---|---|---|
| 6,555,273 B2 | 4/2003 | Tanabe | |
| 6,610,994 B1 * | 8/2003 | Tanabe | 250/559.45 |
| 7,136,159 B2 | 11/2006 | Tsai et al. | |
| 7,292,346 B2 | 11/2007 | De Groot et al. | |
| 7,345,771 B2 | 3/2008 | Hill | |
| 2001/0044052 A1 | 11/2001 | Tanabe | |

FOREIGN PATENT DOCUMENTS

| | | |
|---|---|---|
| JP | 3221848 A | 9/1991 |
| JP | 6201601 A | 7/1994 |
| JP | 831723 A | 2/1996 |
| JP | 8261953 A | 10/1996 |
| JP | 8333125 A | 12/1996 |
| JP | 11264798 A | 9/1999 |
| JP | 200381654 A | 3/2003 |
| JP | 200529452 A | 2/2005 |

OTHER PUBLICATIONS

Chinese Office Action corresponding to Chinese Patent Application No. 200680005281.3 dated Sep. 25, 2009.
Chinese Office Action corresponding to Chinese Patent Application No. 200680005281.3 dated Jul. 2, 1010.
Japanese Office Action dated Apr. 12, 2011 from corresponding Japan Patent Appln. No. 2006-042996.

* cited by examiner

*Primary Examiner* — Michael P Stafira
(74) *Attorney, Agent, or Firm* — Sughrue Mion, PLLC

(57) ABSTRACT

An inspection method of transparent articles wherein presence or absence of optical inhomogeneities within the transparent articles can be accurately inspected is provided. In an inspection method of transparent articles used in photolithography, for inspecting whether or not there are inhomogeneities within transparent articles formed of transparent material wherein optical properties regionally or locally change with regard to exposure light, inspection light having a wavelength of 200 nm or shorter is introduced to the transparent article, and light having a longer wavelength than the inspection light which is regionally or locally emitted is sensed on the optical path over which the inspection light is propagated within the transparent article, thereby detecting presence or absence of optical inhomogeneities within the transparent article.

20 Claims, 8 Drawing Sheets

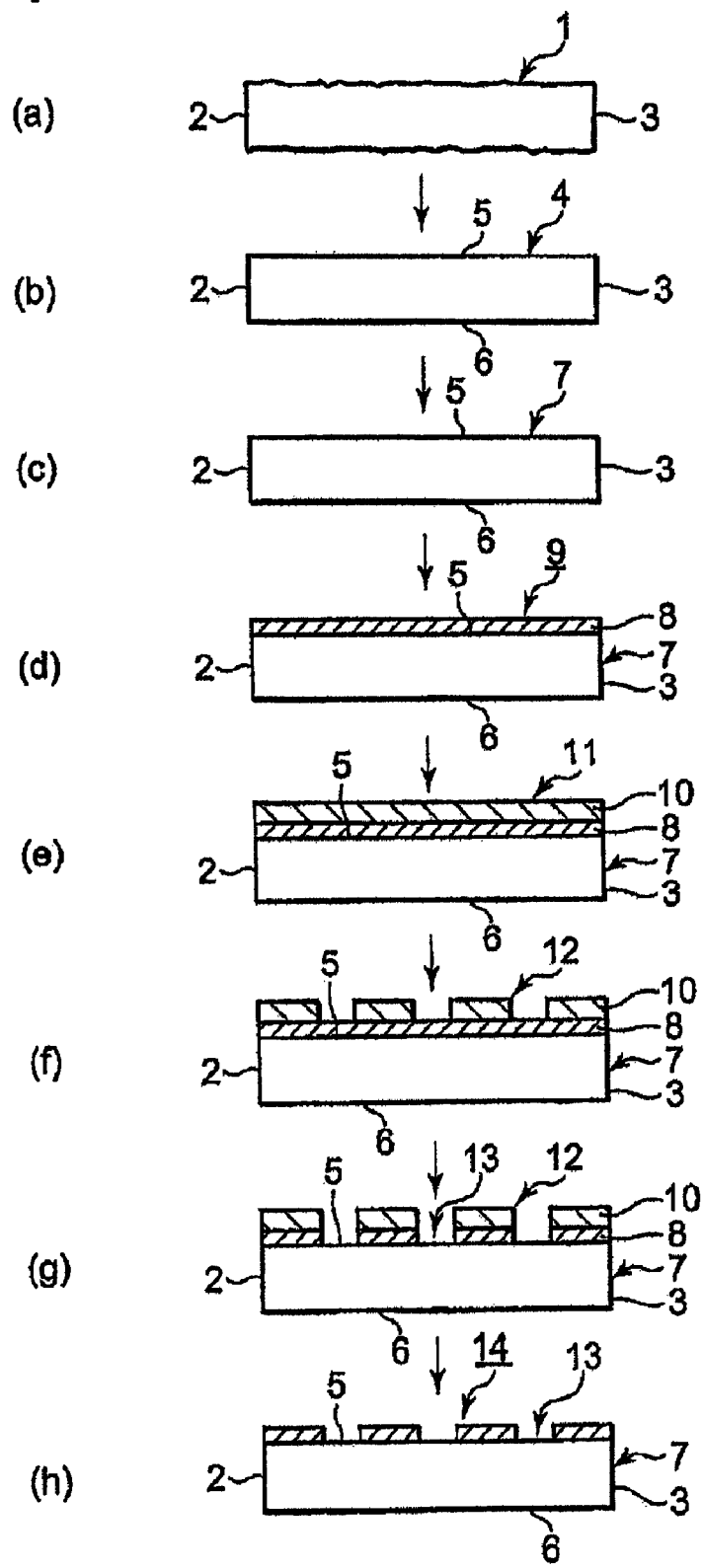
[Fig. 1]

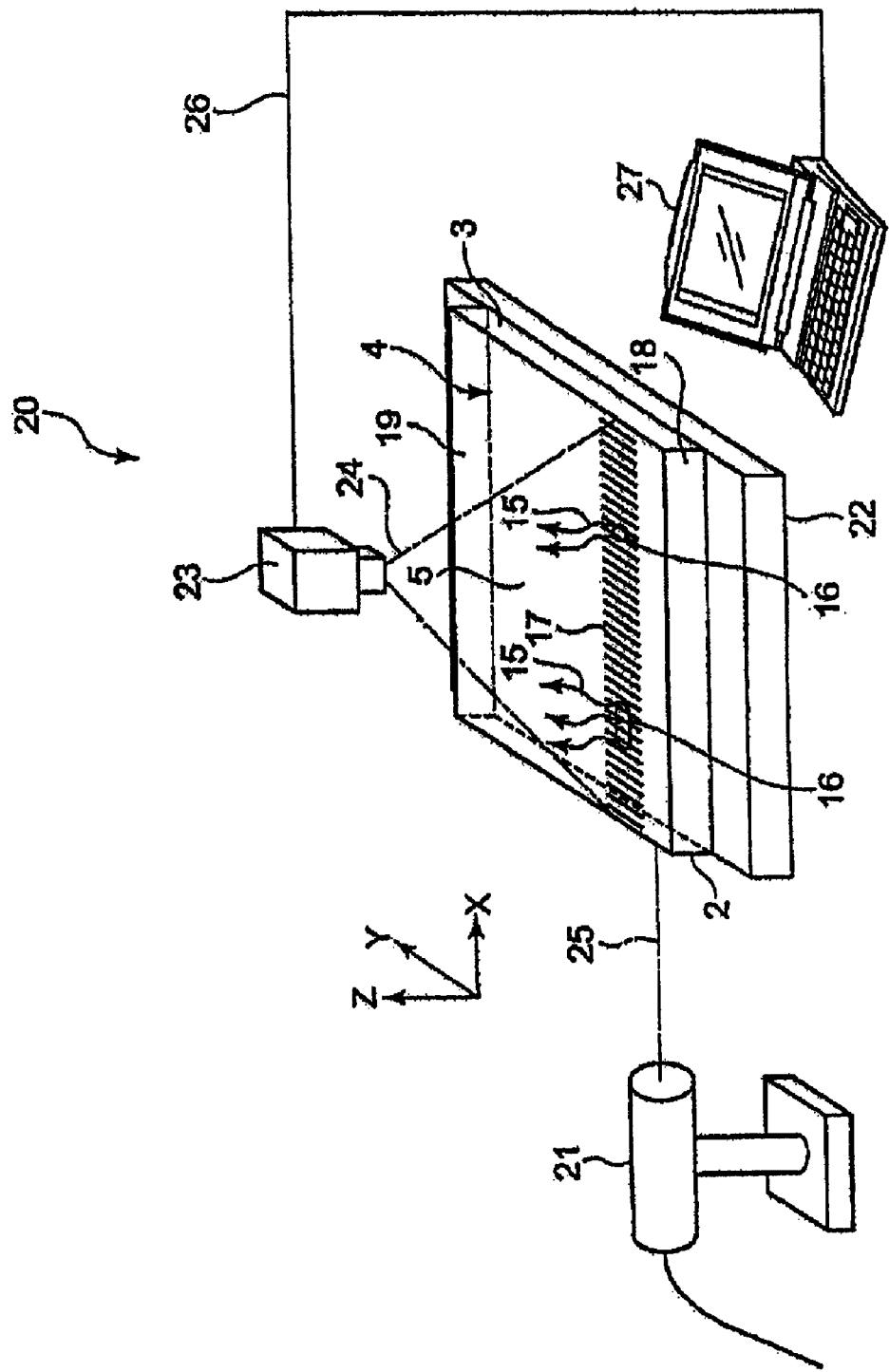
[Fig. 2]

[Fig. 3]
(A)
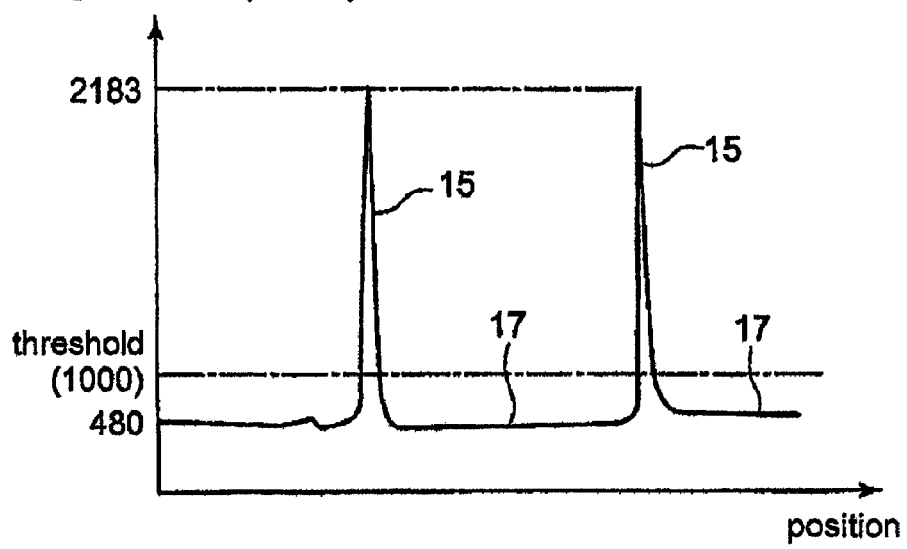
(B)
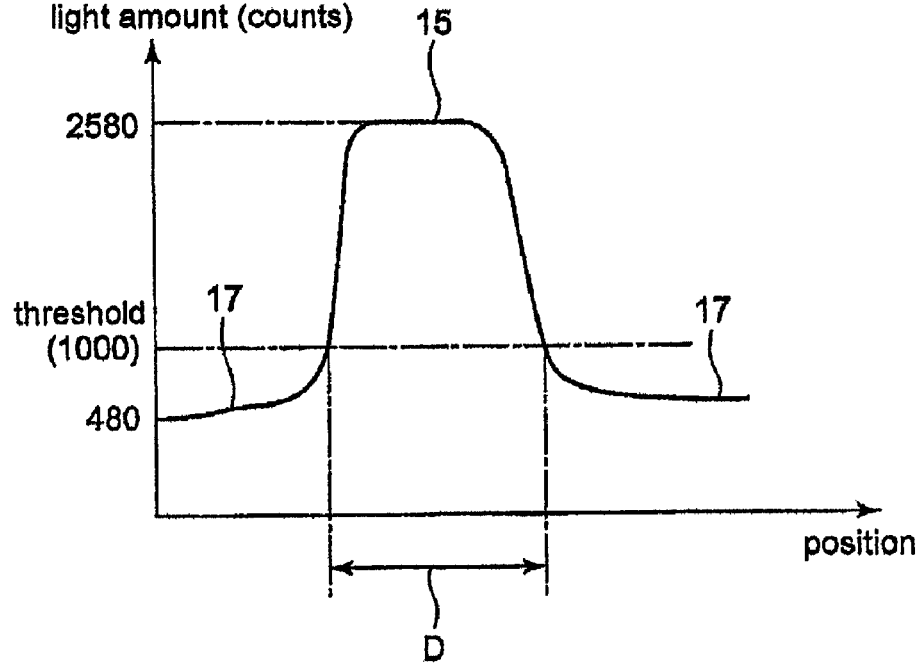

[Fig. 4]
(A)
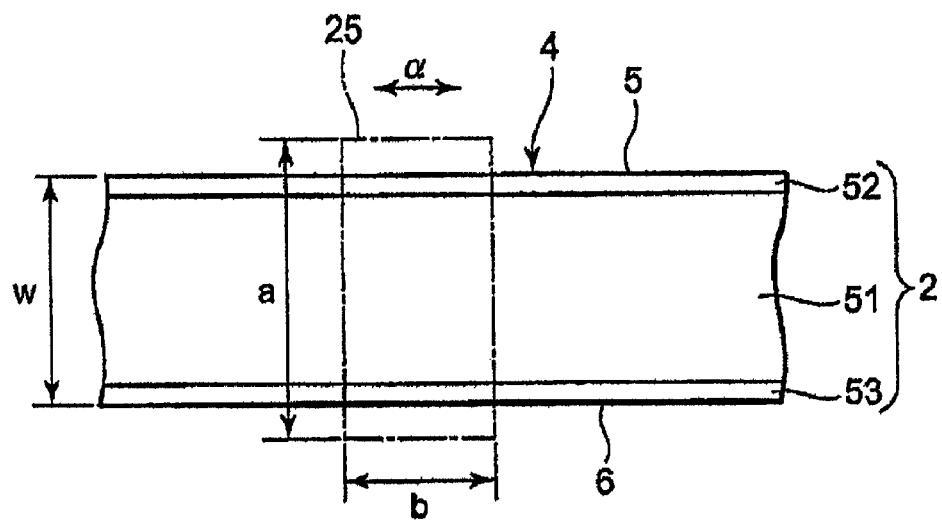
(B)
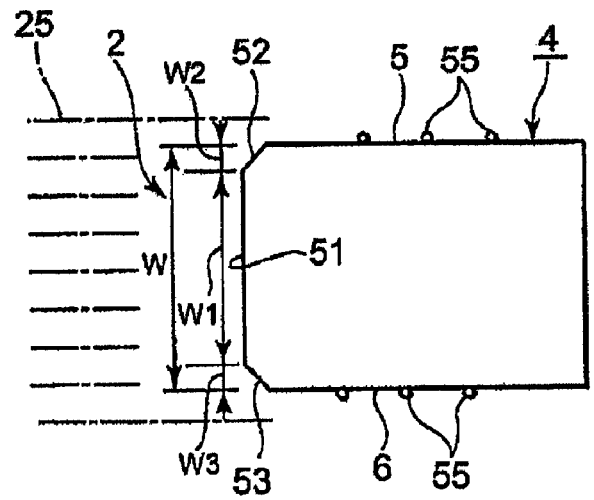

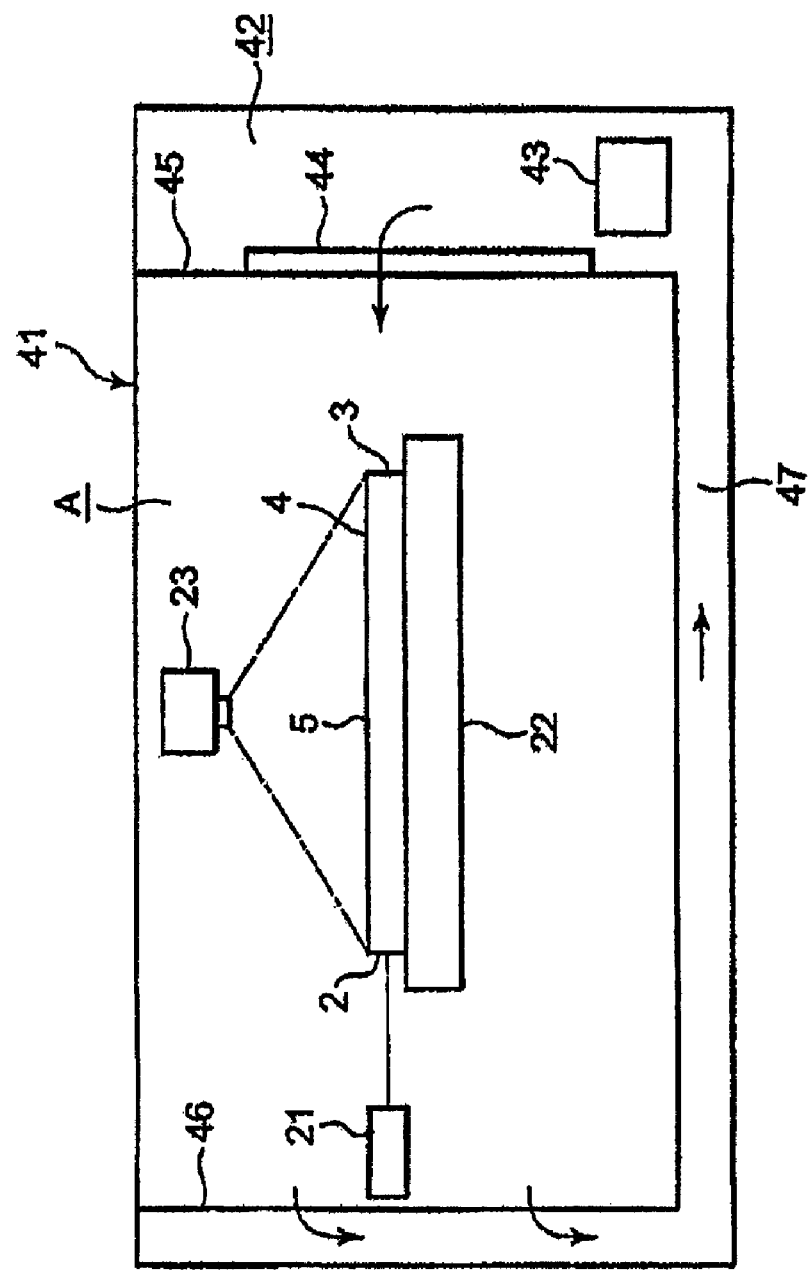
[Fig. 5]

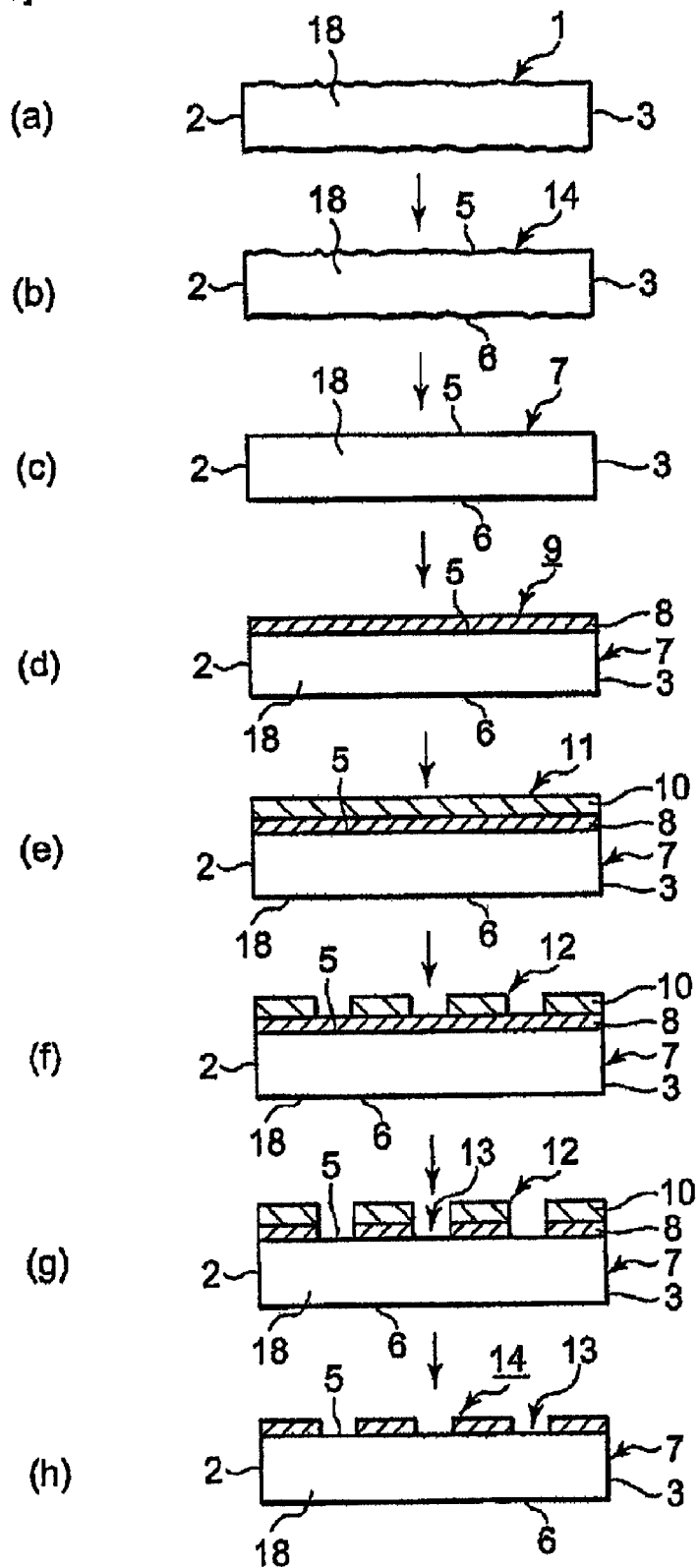

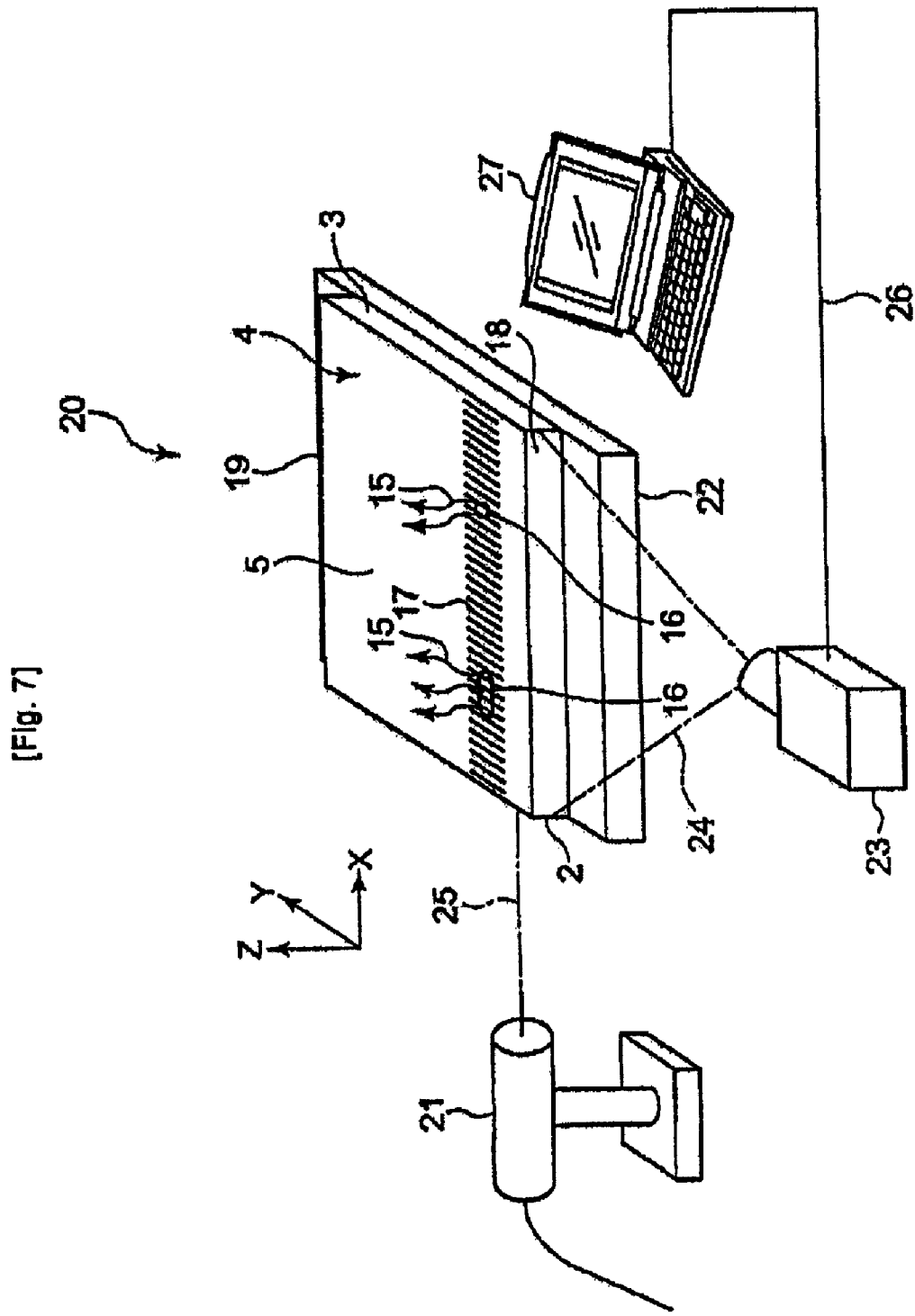
[Fig. 7]

[Fig. 8]
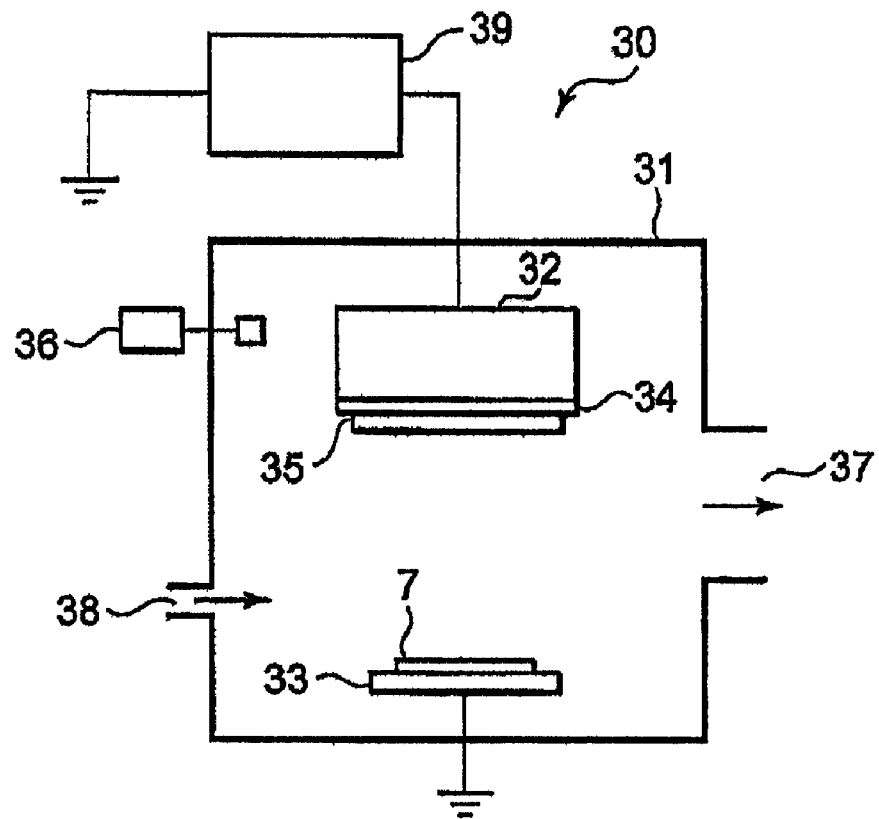
[Fig. 9]
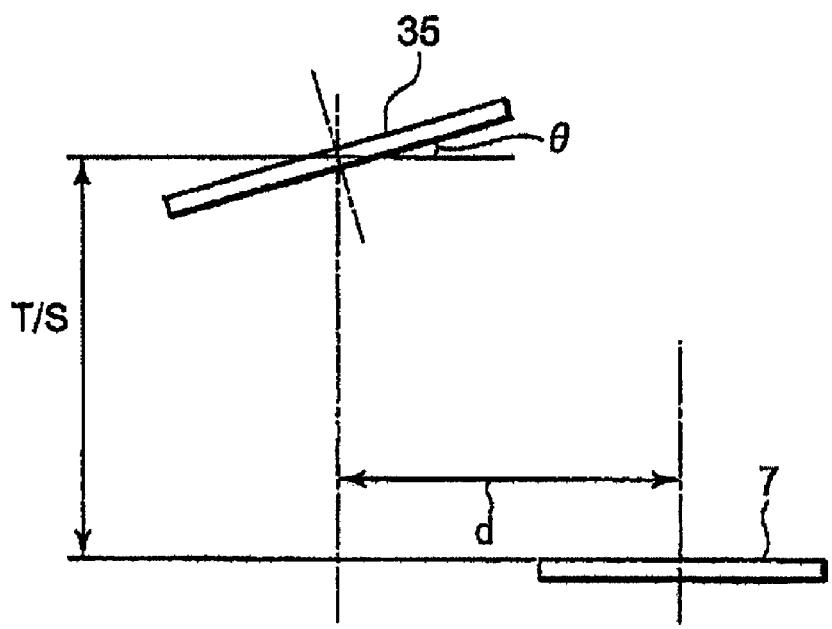

TRANSPARENT ARTICLE

CROSS-REFERENCE TO RELATED APPLICATIONS

This is a Divisional of U.S. application Ser. No. 11/816,617 filed Aug. 17, 2007, which is a 371 of PCT Application No. PCT/JP2006/302612 filed Feb. 15, 2006, and which claims benefit of Japanese Patent Application No. 2005-43134 filed Feb. 18, 2005, Japanese Patent Application No. 2005-228598 filed Aug. 5, 2005 and Japanese Patent Application No. 2005-244044 filed Aug. 25, 2005, the contents of all of which are incorporated herein by reference in their entirety.

TECHNICAL FIELD

The present invention relates to a transparent article formed of a transparent material having transparency as to light having an extremely powerful energy such as an ArF excimer laser or F2 excimer laser for example, regarding presence or absence of inhomogeneity wherein optical properties locally change within the transparent article as to the light, and also relates to a glass substrate inspection method and device, and to a manufacturing method of glass substrates to be used as mask blanks wherein mask blank glass substrates are manufactured following inspection of interior defects of glass substrates, a mask blank manufacturing method using the mask blank glass substrates, and to an exposure mask manufacturing method using the mask blanks, and to the manufacturing method of a semiconductor device using the exposure masks.

BACKGROUND ART

In recent years, improved fineness of patterns formed on semiconductor devices has led to shorter wavelengths of exposure light used for photolithography, i.e., ArF excimer laser (exposure wavelength of 193 nm), and F2 excimer laser (exposure wavelength of 157 nm). With regard to exposure masks used for the photolithography, and mask blanks used for manufacturing the exposure masks, there has been rapid development for opaque films for shielding the above-mentioned exposure wavelengths of exposure light and phase shift films for phase shift thereof, which are formed on transparent substrates for mask blanks (e.g., glass substrates), and various film materials have been proposed.

Also, exposure devices used in photolithography (e.g., steppers) have optical components such as lenses and the like, and materials with little absorption of exposure light, i.e., materials with good optical transparency are used for the optical components.

It is demanded of the mask blank transparent substrates and transparent articles for manufacturing the mask blank transparent substrates (e.g., synthetic quartz glass substrates) and optical components such as lenses and the like used in the exposure devices, that there be no optical inhomogeneity therein (change in optical properties due to defects such as foreign matter, bubbles, and so forth). Patent Document 1 discloses a detect detecting device and detect inspection method for detecting such optical inhomogeneity by irradiating a He—Ne laser into a glass substrate and detecting scattered light scattered by optical uniformity present within the glass substrate, e.g., the interior defects (foreign matter, bubbles, and so forth), thereby detecting the aforementioned optical uniformity.

Patent Document 1: Japanese Unexamined Patent Application Publication (JP-A) No. 8-261953

Patent Document 2: Japanese Unexamined Patent Application Publication (JP-A) No. 8-31723

Patent Document 3: Japanese Unexamined Patent Application Publication (JP-A) No. 2003-81654

PROBLEMS TO BE SOLVED BY THE INVENTION

There are cases wherein, even with transparent substrates (e.g., synthetic quartz glass substrates) and mask blank transparent substrates (e.g., mask blank glass substrates) regarding which determination has been made by such a detect detecting device that there are no optical inhomogeneities (e.g., interior defects), transfer pattern defects occur due to transparent substrates as described later at the time of transferring the pattern wherein a mask pattern for an exposure mask is transferred onto a semiconductor substrate using an ArF excimer laser which is the exposure light, leading to degradation of transfer precision. Also, there are cases wherein, in the same way as described above, transfer pattern defects owing to optical components occur at the time of pattern transfer with the optical components such as lenses and the like used in the exposure device, thereby leading to degradation of transfer precision.

The reason is thought to be that, even in the event that there is no optical change such as scattering when using visible light laser such as the He—Ne laser as the inspection light, at the time of performing actual pattern transfer using high-energy light such as ArF excimer laser and F2 excimer laser as the exposure light, there are optical inhomogeneities (interior defects originated by local striae, inclusions, foreign matter, for example) present in the transparent substrate or optical components, causing regional (or local) change in optical properties (e.g., drop of transmissivity, change in phase difference).

The present invention has been made in light of the above situation, and accordingly it is an object thereof to provide an inspection method for inspecting a transparent article such as optical components of exposure devices and substrates for exposure masks, used in photolithography, regarding presence or absence of inhomogeneity in optical properties greatly affecting pattern transfer to a transfer medium.

Another object of the present invention is to provide a semiconductor device manufacturing method whereby the transfer precision of a pattern transfer onto semiconductor substrates can be suitably realized, an exposure mask and a manufacturing method thereof wherein the transfer precision of pattern transfer onto a transfer medium to manufacture the semiconductor device is suitable, a manufacturing method of a mask blank for manufacturing the exposure mask and a manufacturing method thereof, and a mask blank transparent substrate for manufacturing the mask blank and the manufacturing method thereof.

MEANS TO SOLVE THE PROBLEMS

According to this invention, an inspection method is for inspecting a transparent article formed of a transparent material used for photolithography, regarding presence or absence of inhomogeneity wherein optical properties regionally or locally change within the transparent article as to exposure light; wherein inspection light having a wavelength of 200 nm or shorter is introduced into the transparent article, and light having a wavelength longer than that of the inspection light that has been generated regionally or locally is detected on the optical path over which the inspection light is propagated within the transparent article, thereby inspecting for presence or absence of optical inhomogeneity in the transparent article.

According to this invention, the inspection method is for inspecting a transparent article, wherein the light having a wavelength longer than that of the inspection light has a wavelength exceeding 200 nm and up to 600 nm.

According to this invention, the inspection method is for inspecting a transparent article, wherein the transparent article is either an optical component of an exposure device used for photolithography, or a substrate of an exposure mask used for photolithography.

According to this invention, the inspection method is for inspecting a transparent article, wherein the optical component or the exposure mask substrate are formed of synthetic quartz glass.

According to this invention, the inspection method is for inspecting a transparent article, wherein, at the time of introducing the inspection light to the transparent article, the inspection light is introduced to the transparent article in a state wherein causative substance which causes damage to the surface of the transparent article upon introduction of the inspection light is eliminated from the ambient atmosphere of the transparent article.

According to this invention, the inspection method is for inspecting a transparent article 5, wherein the energy of the inspection light per unit area is 10 $mJ/cm^2$ or greater but 50 $mJ/cm^2$ or smaller per pulse.

According to this invention, a manufacturing method is of a transparent substrate for a mask blank, the method comprising a preparation step for preparing a transparent substrate for a mask blank, having a surface from which inspection light having a wavelength of 200 nm or shorter is introduced; an inspection step wherein inspection light is introduced from one side of the surface, and light having a wavelength longer than that of the inspection light that is generated regionally or locally is detected on the optical path over which the inspection light is propagated within the transparent article, thereby inspecting for presence or absence of optical inhomogeneity in the transparent article; and a determining step for determining whether or not the transparent substrate will generate no transfer pattern defects due to regional or local optical property changes, based on the present or absence of the inhomogeneity.

According to this invention, the manufacturing method is of a transparent substrate for a mask blank, wherein the light having a wavelength longer than that of the inspection light has a wavelength exceeding 200 nm and up to 600 nm.

According to this invention, the manufacturing method is of a transparent substrate for a mask blank, wherein the principal surface of the transparent substrate is subjected to precision polishing following the determining step, thereby obtaining a transparent substrate for a mask blank.

According to this invention, the manufacturing method is of a transparent substrate for a mask blank, wherein, at the time of introducing the inspection light to the transparent article, the inspection light is introduced to the transparent article in a state wherein causative substance which causes damage to the surface of the transparent article upon introduction of the inspection light is eliminated from the ambient atmosphere of the transparent article.

According to this invention, the manufacturing method is of a transparent substrate for a mask blank 0, wherein the surface wherein the inspection light is introduced is a side face orthogonal to the principal surface of the transparent substrate upon which a thin film to serve as a mask pattern is formed.

According to this invention the manufacturing method is of a transparent substrate for a mask blank, wherein, in the inspection step, inspection light having a beam shape greater than the width of the side face is introduced to the surface.

According to this invention, the manufacturing method is of a transparent substrate for a mask blank, wherein the energy of the inspection light per unit area is 10 $mJ/cm^2$ or greater but 50 $mJ/cm^2$ or smaller per pulse.

According to this invention, a manufacturing method is for a mask blank, wherein a thin film to serve as a mask pattern is formed on the principal surface of a transparent substrate for a mask blank obtained by the manufacturing method of a transparent substrate for a mask blank, thereby manufacturing a mask blank.

According to this invention, a manufacturing method is for an exposure mask, wherein the thin film on the mask blank is patterned so as to form a mask pattern on the principal surface of the transparent substrate for a mask blank, thereby manufacturing an exposure mask.

According to this invention, a manufacturing method is for a semiconductor device, wherein an exposure mask obtained by the manufacturing method for an exposure mask is used to transfer a mask pattern formed on an exposure mask onto a resist film to manufacture a semiconductor device.

According to this invention a transparent substrate is for a mask blank, wherein upon introduction of light having a wavelength of 200 nm or shorter from one side of the surface of the transparent substrate, the loss of light having a wavelength longer than the wavelength that is generated regionally or locally within the transparent substrate is 8%/cm or lower within the mask pattern formation region of the transparent substrate.

According to this invention, the transparent substrate is for a mask blank wherein the transparent substrate for a mask blank is a transparent substrate for a phase-shift mask blank.

According to this invention, the transparent substrate is for a mask blank wherein the loss of light having a wavelength longer than the wavelength that is generated regionally or locally within the transparent substrate is 3%/cm or lower within the mask pattern formation region of the transparent substrate.

According to this invention, a mask blank, wherein a thin film to serve as a mask pattern, or a thin film for forming a mask pattern, is formed on the principal surface of the transparent substrate for a mask blank.

According to this invention an exposure mask wherein the thin film to serve as a mask pattern on the mask blank is patterned to form a mask pattern of a thin film pattern on the principal surface of the transparent substrate for a mask blank.

According to this invention an exposure mask wherein the thin film to form a mask pattern on the mask blank is patterned to form a thin film pattern, and the thin film pattern is used as a mask to etch the transparent substrate for a mask blank, thereby forming a mask pattern on the principal surface of the transparent substrate.

ADVANTAGES

With the invention, in an inspection method for inspecting a transparent article formed of a transparent material used for photolithography, regarding presence or absence of inhomogeneity wherein optical properties regionally or locally change within the transparent article as to exposure light; inspection light having a wavelength of 200 nm or shorter is introduced into the transparent article, and light having a wavelength longer than that of the inspection light that is generated regionally or locally is detected on the optical path over which the inspection light is propagated within the transparent article, thereby inspecting for presence or absence of optical inhomogeneity in the transparent article, thereby enabling accurate inspection for presence or absence of interior defects which greatly affect pattern transfer to a transfer medium.

Now, in the event that the transparent article is an optical component of an exposure device used for photolithography, or for manufacturing a substrate of an exposure mask used for photolithography (transparent substrate for a mask blank), the exposure mask manufactured via this substrate for exposure mask and mask blank, and optical component of the exposure device do not have regionally or locally optically inhomogeneous regions, so at the time of using the exposure mask or optical component and exposure light to transfer the mask pattern of the exposure mask onto the transfer medium, there is no region wherein optical properties change (e.g., drop of transmissivity) due to regionally or locally optically inhomogeneity, so excellent transfer precision can be obtained without transfer pattern defects on the transfer medium due to adverse affects thereof on the pattern transfer.

With the invention, accurate inspection for presence or absence of interior defects which greatly affect pattern transfer to a transfer medium can be performed while preventing damage to the surface of the transparent article.

At the time of introducing the inspection light to the transparent article, the inspection light is introduced to the transparent article in a state wherein causative substance (e.g., floating particles) or the like which causes damage to the surface of the transparent article upon introduction of the inspection light is eliminated from the ambient atmosphere of the transparent article, so damage to the surface which occurs due to adhering matter and deposited matter adhering to the surface of the transparent article regionally or locally making the temperature of the surface high can be prevented.

With the invention, the energy of the inspection light per unit area is 10 mJ/cm$^2$ or greater but 50 mJ/cm$^2$ or smaller per pulse, so generation of plasma at the surface of the transparent article due to the inspection light can be avoided, and the intensity of wavelengths having a longer wavelength than the inspection light which is generated from optical inhomogeneities upon introduction of the inspection light is sufficiently ensured, so detection precision of inhomogeneity can be maintained high.

With the invention, a transparent substrate for a mask blank is manufactured via a preparation step for preparing a transparent substrate for a mask blank, having a surface from which inspection light having a wavelength of 200 nm or shorter is introduced; an inspection step wherein inspection light is introduced from one side of the surface, and light having a wavelength longer than that of the inspection light that is generated regionally or locally is detected on the optical path over which the inspection light is propagated within the transparent article, thereby inspecting for presence or absence of optical inhomogeneity in the transparent article; and a determining step for determining whether or not the transparent substrate will generate no transfer pattern defects due to regional or local optical property changes, based on the presence or absence of the inhomogeneity, so there is no region wherein optical properties change (e.g., drop of transmissivity) due to regionally or locally optically inhomogeneity, and excellent transfer precision can be obtained without transfer pattern defects on the transfer medium due to adverse affects thereof on the pattern transfer.

With the invention optical in homogeneity of the transparent substrate is detected at an early stage prior to precision polishing of the principal surface in the manufacturing process of the transparent substrate for a mask blank, so the principal surface is subjected to precision polishing only for transparent substrates wherein there is no optical inhomogeneity, thereby avoiding the waste of performing precision polishing on transparent substrates with optical inhomogeneity.

With the invention, a transparent substrate for a mask blank with no optical inhomogeneity which greatly affects pattern transfer to a transfer medium can be obtained without damage to the surface of the transparent substrate for a mask blank due to introduction of inspection light.

With the invention, in addition to the advantages obtained by the invention, there is the advantage of removing foreign matter and contaminants adhering to the principal surface of the transparent substrate for a mask blank.

With the invention, a transparent substrate for a mask blank with no optical inhomogeneity which greatly affects pattern transfer to a transfer medium can be obtained without damage due to generation of plasma at the surface of the transparent substrate for a mask blank due to introduction of inspection light.

With the invention, a transparent substrate for a mask blank obtained by the manufacturing method of a transparent substrate for a mask is used to manufacture a mask blank, the thin film on the mask blank is patterned so as to manufacture an exposure mask, and the exposure mask is used to manufacture a semiconductor device. Accordingly, at the time of using the exposure mask to transfer the mask pattern of the exposure mask onto the transfer medium (semiconductor substrate), there is no region wherein optical properties change (e.g., drop of transmissivity) due to regionally or locally optically inhomogeneity in the transparent substrate used for the exposure mask, so transfer precision can be improved without transfer pattern defects on the transfer medium due to adverse affects thereof on the pattern transfer.

BRIEF DESCRIPTION OF THE DRAWINGS

FIG. 1 A manufacturing process diagram illustrating an embodiment of the manufacturing method of a glass substrate for a mask blank, manufacturing method for a mask blank, and manufacturing method for an exposure mask, according to the present invention.

FIG. 2 A perspective view illustrating an embodiment of a defect inspection device for the glass substrate according to the present invention.

FIG. 3 A graph illustrating intensity distribution of received light subjected to image processing with a computer.

FIG. 4 Views showing ArF excimer laser light guided from a laser irradiation device shown in FIG. 2 and a synthetic quartz glass substrate, wherein (A) is a frontal view and (B) is a side view.

FIG. 5 A schematic frontal view illustrating the overall configuration of the defect inspection device in FIG. 2.

FIG. 6 A manufacturing process diagram illustrating another embodiment of the manufacturing method of a glass substrate for a mask blank, manufacturing method for a mask blank, and manufacturing method for an exposure mask, according to the present invention.

FIG. 7 A perspective view illustrating another embodiment of the defect inspection device for the glass substrate according to the present invention.

FIG. 8 A schematic side view illustrating a sputtering device used in the manufacturing process of the mask blank in FIG. 1.

FIG. 9 A side view illustrating the position relation between the sputtering target and glass substrate for mask blank in FIG. 8.

REFERENCE NUMERALS 20 defect inspecting device
21 laser irradiation device
22 XYZ stage
23 CCD camera
24 detection field
26 USB cable
27 computer
4 synthetic quartz glass substrate
16 interior defect

BEST MODE FOR CARRYING OUT THE INVENTION

As specific means for solving the above problems, the present invention employs the following configuration.

(Configuration 1-1)

A defect inspection method for a glass substrate, wherein light of an exposure wavelength is introduced from one side of a surface of a glass substrate, light of a wavelength longer than the exposure wavelength that is generated at interior defects of the glass substrate by the introduced light of the exposure wavelength is received at the other side of the surface, and interior defects of the glass substrate are detected based on the amount of light received.

(Configuration 1-2)

The defect inspection method for a glass substrate according to Configuration 1-1, wherein the wavelength of the light introduced into the glass substrate is 200 nm or shorter.

(Configuration 1-3)

A defect inspection device for a glass substrate, including light introducing means for introducing light of an exposure wavelength from one side of a surface of a glass substrate, light receiving means for receiving light of a wavelength longer than the exposure wavelength that is generated at interior defects of the glass substrate by the introduced light of the exposure wavelength, at the other side of the surface, and detecting means for detecting interior defects of the glass substrate, based on the amount of light received by the light receiving means.

(Configuration 1-4)

The defect inspection device for a glass substrate according to Configuration 1-3, wherein the wavelength of the light introduced into the glass substrate is 200 nm or shorter.

(Configuration 1-5)

A manufacturing method for a glass substrate for a mask blank, including: a preparation step for preparing a synthetic quartz glass substrate having a surface from which light of an exposure wavelength is introduced; and a detecting step wherein light of the exposure wavelength is introduced from one side of the surface and light of a wavelength longer than the exposure wavelength that is generated at interior defects of the glass substrate by the introduced light of the exposure wavelength is received at the other side of the surface, whereby interior defects of the glass substrate are detected based on the intensity of light received; wherein glass substrates for mask blanks are manufactured using the synthetic quartz glass substrates regarding which interior defects have not been detected in the detecting step.

(Configuration 1-6)

The manufacturing method for a glass substrate for a mask blank according to Configuration 1-5, wherein the wavelength of the light introduced into the glass substrate is 200 nm or shorter.

(Configuration 1-7)

The manufacturing method for a glass substrate for a mask blank according to Configuration 1-5 or Configuration 1-6, wherein the principal surface of the synthetic quartz glass substrate is subjected to precision polishing following the detecting step, thereby obtaining a glass substrate for a mask blank.

(Configuration 1-8)

A manufacturing method for a mask blank, wherein a thin film to serve as a mask pattern is formed on the principal surface of the glass substrate for a mask blank obtained by the manufacturing method of a glass substrate for a mask blank according to any one of Configuration 1-5 through Configuration 1-7.

(Configuration 1-9)

A manufacturing method for an exposure mask wherein the thin film on the mask blank according to Configuration 1-8 is patterned so as to form a mask pattern on the principal surface of the glass substrate for a mask blank, thereby manufacturing an exposure mask.

With the invention according to any one of Configuration 1-1 through Configuration 1-4, light of an exposure wavelength is introduced from one side of a surface of a glass substrate, light of a wavelength longer than the exposure wavelength that is generated at interior defects of the glass substrate by the introduced light of the exposure wavelength is received at the other side of the surface, and interior defects of the glass substrate are detected based on the intensity of light received, so using light of an exposure wavelength for inspecting interior defects of glass substrates enables interior defects which would lead to transfer pattern defects at the time of pattern transfer to be detected well.

Now, in the event that the glass substrate is for manufacturing a glass substrate for a mask blank, there are no interior defects in an exposure mask glass substrate manufactured via the glass substrate for a mask blank and the mask blank, so at the time of performing pattern transfer wherein the mask pattern of the exposure mask is transferred onto a transfer medium using the exposure mask and exposure light, there is no region wherein optical properties regionally change (e.g., drop of transmissivity), so excellent transfer precision can be obtained without transfer pattern defects on the transfer medium due to adverse affects thereof on the pattern transfer.

With the invention according to Configuration 1-5 or Configuration 1-6, light of the exposure wavelength is introduced from one side of the surface of a synthetic quartz glass substrate, light of a wavelength longer than the exposure wavelength that is generated at interior defects of the glass substrate by the introduced light of the exposure wavelength is received at the other side of the surface, interior defects of the glass substrate are detected based on the intensity of light received, and glass substrates for mask blanks are manufactured using the synthetic quartz glass substrates regarding which interior defects have not been detected, so there are no interior defects in the glass substrates for exposure masks manufactured via the glass substrate for a mask blank and the mask blank. Accordingly, at the time of performing pattern transfer wherein the mask pattern of the exposure mask is transferred onto a transfer medium using the exposure mask and exposure light, there is no region wherein optical properties regionally change (e.g., drop of transmissivity), so excellent transfer precision can be obtained without transfer pattern defects due to adverse affects thereof on the pattern transfer.

With the invention according to Configuration 1-7, interior defects in the quartz glass substrate are detected at an early stage prior to precision polishing of the principal surface in the manufacturing process of the glass substrate for a mask blank, so the principal surface is subjected to precision polishing only for quartz glass substrates wherein there is no interior defect, thereby avoiding the waste of performing precision polishing on quartz glass substrates with interior defects.

With the invention according to Configuration 1-8 or Configuration 1-9, a glass substrate for a mask blank obtained by the manufacturing method of a glass substrate for a mask blank according to any one of Configurations 1-5 through 1-7 is used to manufacture a mask blank, the thin film on the mask blank is patterned so as to manufacture an exposure mask, so at the time of using the exposure mask to transfer the mask pattern of the exposure mask onto the transfer medium, there is no region wherein optical properties regionally change (e.g., drop of transmissivity) since a quartz glass substrate wherein there are no interior defects is used, and excellent transfer precision can be obtained without transfer pattern defects due to adverse affects thereof on the pattern transfer.

As specific means for solving the above problems, the present invention further employs the following configuration.

(Configuration 2-1)

A manufacturing method for a glass substrate for a mask blank including: a preparation step for preparing a synthetic quartz glass substrate having a surface from which short-wavelength light having a wavelength of 200 nm or shorter is introduced; and a detecting step for introducing the short-wavelength light from the surface of the synthetic quartz glass substrate, receiving long-wavelength light of a wavelength longer than the short-wavelength light that is generated at interior defects of the glass substrate at the other side of the surface, and detecting the interior defects based on the received long-wavelength light; with glass substrates for mask blanks being manufactured using the quartz glass substrates in which no interior defects are detected in the detecting step; wherein, in the detecting step, at the time of introducing the short-wavelength light to the quartz glass substrate, the short-wavelength light is introduced to the quartz glass substrate in a state in which causative substance which causes damage to the surface of the glass substrate upon introduction of the short-wavelength light is eliminated from the ambient atmosphere of the glass substrate.

(Configuration 2-2)

The manufacturing method for a glass substrate for a mask blank according to Configuration 2-1, wherein the state in which causative substance is eliminated from the ambient atmosphere of the quartz glass substrate is an atmosphere wherein clean air circulates.

(Configuration 2-3)

The manufacturing method for a glass substrate for a mask blank according to Configuration 2-1 or Configuration 2-2, wherein the atmosphere wherein clean air circulates is an atmosphere of a cleanness exceeding that of ISO Class 5.

(Configuration 2-4)

The manufacturing method for a glass substrate for a mask blank according to any one of Configuration 2-1 through Configuration 2-3, wherein the atmosphere wherein clean air circulates is generated by air passing through a chemical filter.

(Configuration 2-5)

The manufacturing method for a glass substrate for a mask blank according to any one of Configuration 2-1 through Configuration 2-4, wherein the maximum height (Rmax) of the surface of the synthetic quartz substrate into which the short-wavelength light is introduced is 0.5 μm or lower.

(Configuration 2-6)

A manufacturing method for a mask blank, wherein a thin film to serve as a mask pattern is formed on the principal surface of the glass substrate for a mask blank obtained by the manufacturing method of a glass substrate for a mask blank according to any one of Configuration 2-1 through Configuration 2-5.

(Configuration 2-7)

A manufacturing method for an exposure mask wherein the thin film on the mask blank according to Configuration 2-6 is patterned so as to form a mask pattern on the principal surface of the glass substrate for a mask blank, thereby manufacturing an exposure mask.

With the invention according to any one of Configuration 2-1 through Configuration 2-5, short-wavelength light having a wavelength of 200 nm or shorter is introduced to the synthetic quartz glass substrate, and the short-wavelength light is used for inspection of interior defects in the synthetic quartz glass substrate (glass substrate for a mask blank), so interior defects which would lead to transfer pattern defects at the time of pattern transfer using the exposure mask manufactured from this glass substrate, and exposure light, can be detected well.

At the time of introducing the short-wavelength light which is the inspection light to the synthetic quartz glass substrate, the inspection light is introduced to the glass substrate in a state wherein causative substance (e.g., floating particles) or the like which causes damage to the surface of the glass substrate upon introduction of the short-wavelength light is eliminated from the ambient atmosphere of the glass substrate, so damage to the surface which occurs due to adhering matter and deposited matter adhering to the surface of the synthetic quartz glass substrate regionally or locally making the temperature of the surface high can be prevented. Particularly, forming the maximum height (Rmax) of the surface of the synthetic quartz substrate into which the inspection light is introduced so as to be 0.5 μm or lower makes adhesion of causative substances which generate damage more difficult, so damage to the surface can be further prevented.

Also, according to the Configuration 2-6 or Configuration 2-7, a mask blank is manufactured using the glass substrate for a mask blank obtained by the manufacturing method for a glass substrate for a mask blank according to any one of Configuration 2-1 through Configuration 2-5, and the thin film on the mask blank is patterned so as to form an exposure mask. Accordingly, at the time of pattern transferring wherein the mask pattern of the exposure mask is transferred to a transfer medium using the exposure mask, a synthetic quartz glass substrate wherein there are no interior defects and no damage on the surface is used, so there is no region where optical properties regionally change (e.g., drop of transmissivity) due to the interior defects or the damage, and transfer precision can be improved without adverse effect on pattern transfer leading to transfer pattern defects.

Also, as specific means for solving the above problems, the present invention employs the following configuration.

(Configuration 3-1)

A manufacturing method for a glass substrate for a mask blank including: a preparation step for preparing a synthetic quartz glass substrate having a surface including one end face from which short-wavelength light having a wavelength of 200 nm or shorter is introduced; and a detecting step for introducing the short-wavelength light from the one end face, receiving long-wavelength light of a wavelength longer than the short-wavelength light that is generated at interior defects of the glass substrate at the other side of the surface, and detecting the interior defects based on the received long-wavelength light; with glass substrates for mask blanks being manufactured using the quartz glass substrates in which no interior defects have been detected in the detecting step; wherein, in the detecting step, the short-wavelength light having a beam shape larger than the width of the one end face is introduced to the one end face.

(Configuration 3-2)

The manufacturing method for a glass substrate for a mask blank according to Configuration 3-1, wherein the end face is a side face orthogonal to the principal surface of the glass substrate upon which the thin film to serve as the mask pattern is to be formed, and a chamfered face between the side face and the principal surface.

(Configuration 3-3)

The manufacturing method for a glass substrate for a mask blank according to Configuration 3-1 or Configuration 3-2, wherein the energy of the short-wavelength light per unit area is 10 mJ/cm$^2$ or greater but 50 mJ/cm$^2$ or smaller (per pulse).

(Configuration 3-4)

The manufacturing method for a glass substrate for a mask blank according to any one of Configuration 3-1 through Configuration 3-3, wherein, at the one end face of the synthetic quartz glass substrate, the short-wavelength light is scanned in the longitudinal direction of the one end face.

(Configuration 3-5)

A manufacturing method for a mask blank, wherein a thin film to serve as a mask pattern is formed on the principal surface of the glass substrate for a mask blank obtained by the manufacturing method of a glass substrate for a mask blank according to any one of Configuration 3-1 through Configuration 3-4.

(Configuration 3-6)

A manufacturing method for an exposure mask wherein the thin film on the mask blank according to Configuration 3-5 is patterned so as to form a mask pattern on the principal surface of the glass substrate for a mask blank, thereby manufacturing an exposure mask.

With the invention according to Configuration 3-1 or Configuration 3-2, short-wavelength light having a wavelength of 200 nm or shorter is introduced to the synthetic quartz glass substrate, and the short-wavelength light is used for inspection of interior defects in the synthetic quartz glass substrate (glass substrate for a mask blank), so interior defects which would lead to transfer pattern defects at the time of pattern transfer using the exposure mask manufactured from this glass substrate, and exposure light, can be detected well.

Also, the beam shape of the short-wavelength light is set to be larger than the width of the one end face of the synthetic quartz glass substrate into which the short-wavelength light is introduced, so the energy (per pulse) of the short-wavelength light per unit area at the one end face is not too strong, thereby preventing plasma from occurring around the one end face. Consequently, a situation wherein contamination or foreign matter or the like adhering to the one end face damages the one end face due to plasma can be prevented.

With the invention according to Configuration 3-3, the energy of the short-wavelength light per unit area introduced to the one end face of the synthetic quartz glass substrate is 10 mJ/cm$^2$ or greater but 50 mJ/cm$^2$ or smaller (per pulse), so generation of plasma at the one end face due to this short-wavelength light can be avoided, and also the intensity of the long-wavelength light generated at interior defects due to introduction of the short-wavelength light is sufficiently ensured, and accordingly reliability of defect detection precision can be maintained.

With the invention according to Configuration 3-4, at the one end face of the synthetic quartz glass substrate, the short-wavelength light is scanned in the longitudinal direction of the one end face, so the short-wavelength light is irradiated on both principal surfaces contiguous to this one end face. Accordingly, particles and contaminants adhering to these both principal surfaces can be removed by the short-wavelength light.

Also, according to the Configuration 3-5 or Configuration 3-6, a mask blank is manufactured using the glass substrate for a mask blank obtained by the manufacturing method for a glass substrate for a mask blank according to any one of Configuration 3-1 through Configuration 3-4, and the thin film on the mask blank is patterned so as to form an exposure mask. Accordingly, at the time of pattern transferring wherein the mask pattern of the exposure mask is transferred to a transfer medium using the exposure mask, a synthetic quartz glass substrate wherein there are no interior defects and no damage on the surface is used, so there is no region where optical properties regionally change (e.g., drop of transmissivity) due to the interior defects or the damage, and transfer precision can be improved without adverse effect on pattern transfer leading to transfer pattern defects.

Now, the best mode for carrying out the invention for the manufacturing method for a glass substrate for a mask blank, the manufacturing method for a mask blank, and the manufacturing method for an exposure mask, will be described with reference to the drawings, by way of example of a transparent substrate for a mask blank, more specifically a glass substrate for a mask blank. Note that in the following, the exposure light and inspection light will be described as an ArF excimer laser light (wavelength: 193 nm) with an exposure light wavelength and inspection light wavelength of 200 nm or shorter.

[A] Manufacturing Method for Glass Substrate for Mask Blank

With reference to FIG. 1, a synthetic quartz glass plate 1 (FIG. 1(*a*)) cut out to a size of approximately 152 mm×approximately 152 mm×approximately 6.5 mm or approximately 152.4 mm×approximately 152.4 mm×approximately 6.85 mm from a synthetic quartz glass ingot manufactured according to a manufacturing method disclosed in Patent Document 2 (Japanese Unexamined Patent Application Publication No. 8-31723) or Patent Document 3 (Japanese Unexamined Patent Application Publication No. 2003-81654) is subjected to chamfering, and next, the principal surfaces 5 and 6 which are the surfaces of the synthetic quartz glass plate 1 and the end faces 2 and 3 (end faces are formed of the side faces orthogonal to the principal surfaces 5 and 6, and chamfered faces (not shown) formed between the principal surfaces and the side faces) are polished to a mirror surface of a degree where inspection light (ArF excimer laser light) which is also exposure light wavelength light can be introduced, thereby preparing a synthetic quartz glass substrate 4 (FIG. 1 (*b*)). In this preparation step, the surface roughness Ra (arithmetic average roughness) of the principal surfaces 5 and 6 of the synthetic quartz glass substrate 4 is approximately 0.5 nm or smaller, and the surface roughness Ra (arithmetic average roughness) of the end faces 2 and 3 (side faces and chamfered faces) is approximately 0.03 nm or smaller.

Next, a detecting step is performed wherein the synthetic quartz glass substrate 4 is mounted on a defect detecting device 20 for glass substrates shown in FIG. 2, the ArF excimer laser light is introduced from one end face 2 of the synthetic quartz glass substrate 4, and light (fluorescence) 15 of a wavelength longer than that of the ArF excimer laser light, that is generated by an interior defect 16 which is optical inhomogeneity present within the synthetic quartz glass substrate 4 is received by photoreceptor means (CCD camera 23) from one principal surface 5 of the synthetic quartz glass substrate 4, along with light (fluorescence) 17 of a wavelength longer than that of the ArF excimer laser light generated by regions other than the interior defects 16 of the synthetic quartz glass substrate 4, thereby detecting the interior defects 16 based on difference in light amount (intensity) between the received light 15 and 17.

Now, of the interior defects 16 present in the synthetic quartz glass substrate 4, there are interior defects 16 such as local striae, inclusions, foreign matter, and so forth, which are not problematic in the case that the exposure light is of an exposure light source exceeding a wavelength of 200 nm (e.g., KrF excimer laser (exposure light wavelength: 248 nm), but are problematic in cases of exposure light wavelength of 200 nm or shorter as with ArF excimer laser. These interior defects 16 all cause regional or local optical property changes (e.g., drop of transmissivity or change in phase difference) at the time of pattern transfer wherein the mask pattern of the exposure mask 14 is transferred onto a transfer medium using the exposure mask 14 manufactured from the synthetic quartz glass substrate 4 via the mask blank glass substrate 7 and mask blank 9, and the exposure light of which the exposure light wavelength is 200 nm or shorter. This leads to adverse effects on the pattern transfer and degrading transfer precision. This ultimately becomes a transfer pattern defect of the transfer medium (e.g., semiconductor device) (in the semiconductor medium, a circuit pattern defect).

The aforementioned "local striae" is a region wherein a metal element has become melted into the synthetic quartz glass in minute quantities at the time of synthesizing the synthetic quartz glass. In the event that there is such local striae in the glass substrate 7 for the mask blank for the exposure mask 14, transmissivity will drop 20 to 40% at the time of pattern transfer, degrading transfer precision, and ultimately resulting in a transfer pattern defect. Also, the aforementioned "inclusions" is a region wherein a metal element has become melted into the synthetic quartz glass in quantities greater than with local striae. In the event that there is such contents in the glass substrate 7 for the mask blank for the exposure mask 14, transmissivity will drop approximately 40 to 60% at the time of pattern transfer, degrading transfer precision, and ultimately resulting in a transfer pattern defect. On the other hand, "foreign matter" is an oxygen-excessive region wherein oxygen has become melted in the synthetic quartz glass in excessive quantities, and does not recover following irradiation of high-energy light. In the event that there is such foreign matter in the glass substrate 7 for the mask blank for the exposure mask 14, transmissivity will drop approximately 5 to 15% at the time of pattern transfer, deteriorating transfer precision, and ultimately resulting in a transfer pattern defect. Interior defects 16 which are regional optical inhomogeneities which cause transfer pattern defects at the time of pattern transfer are not restricted to the aforementioned "local striae", "inclusions", and "foreign matter". Optical inhomogeneity wherein loss due to fluorescence generated locally or regionally within the substrate at the time of introducing light, having a wavelength of 200 nm or shorter which is the inspection light or exposure light, to the glass substrate for a mask blank, exceeds 8%/cm, should be taken as an interior defect 16. That is to say, mask blank glass substrates 7 with optical loss within the mask blank glass substrate 7 of 8%/cm or less should be selected in the detecting step. Particularly, in the case of mask blank glass substrates used for phase shift masks, mask blank glass substrates 7 with optical loss of 3% or less should be selected in the detecting step.

An interior defect 16 which causes regional or local changes in optical properties which lead to the aforementioned transfer pattern defects, will generate light (fluorescence) 15 having a wavelength longer than the wavelength of the ArF excimer laser light when introducing the ArF excimer laser to the mask blank glass substrate 7. Wavelengths of the fluorescence 15 generated from the interior defect 16 which will become a transfer pattern defect are longer than 200 nm but 600 nm or shorter, and include violet (wavelength of 400 to 435 nm), blue (wavelength of 435 to 480 nm), cyan (wavelength of 480 to 490 nm), blue-green (wavelength of 490 to 500 nm), green (wavelength of 500 to 560 nm), yellow-green (wavelength of 500 to 580 nm), and yellow (wavelength of 580 to 595 nm). Identification of interior defects 16 by such fluorescence can be made by visually recognizing difference in color between the light 15 and light 17, or detecting difference in spectral properties and/or quantity of light with a spectroscope.

A defect inspecting device 20 for the glass substrate on which inspection step is to be performed is for sensing or detecting the above-described interior defects 16 (regional striae, inclusions, foreign matter, etc., causing local change in optical properties at the time of pattern transfer). The defect inspecting device 20 includes a laser irradiation device 21 serving as light introducing means for introducing ArF excimer laser light which is light of the exposure wavelength (i.e., light of the same wavelength as the exposure wavelength) from the end face 2 of the synthetic quartz glass substrate 4, and XYZ stage 22 upon which the synthetic quartz glass substrate 4 is placed in moved in the X direction, Y direction, and Z direction, as to the laser light emitted from the laser irradiation device 21, and a CCD device and a lens for widening the detection range of the CCD device (both unshown) disposed on the principal surface 5 side of the synthetic quartz glass substrate 4 placed on the XYZ stage 22, and has a CCD camera (line sensor camera) 23 serving as photoreceptor means having a detection field 24 over the entire range of the width direction of the synthetic quartz glass substrate 4 (i.e., the irradiation direction of the laser light irradiated from the laser irradiation device 21), and a computer 27 serving as detecting means, connected to the CCD camera 23 using a USB cable 26.

The laser irradiation device 21 sequentially introduces the ArF excimer laser light from each position in the Y direction at the end face 2 of the synthetic quartz glass substrate 4 (i.e., the longitudinal direction of the end face 2), while the XYZ stage 22 moves the synthetic quartz glass substrate 4 in the Y direction. The laser irradiation device 21 may be that which emits ArF excimer laser light of a beam shape of 7.0 mm×4.0 mm which is larger than the width of the end face 2 for example, energy of 6 mJ per pulse, energy per unit area of 21.4 mJ/cm$^2$, and a frequency of 50 Hz, to the end face 2 which has been polished to a mirror. Also, the CCD camera 23 receives and captures light from the principal surface 5 side of the synthetic quartz glass substrate 4 for each position in the Y direction of the synthetic quartz glass substrate 4, regarding the light 15 and 17 having a wavelength longer than the wavelength $\lambda 1$, which the synthetic quartz glass substrate 4 emits due to the ArF excimer laser light (wavelength of $\lambda 1$) being irradiated into each position in the Y direction at the end face 2 of the synthetic quartz glass substrate 4. With the present embodiment, the CCD camera 23 is a monochrome camera which receives and captures contrast of the light 15 and 17.

The computer 27 inputs the images from the CCD camera 23 and performs image processing for each position in the Y direction of the synthetic quartz glass substrate 4, and analyzes the quantity of light (intensity) of the light 15 and 17 received by the CCD camera 23 with regard to the X directional position of the synthetic quartz glass substrate 4, for each position in the Y direction of the synthetic quartz glass substrate 4. That is to say, in the event that the quantity of light of the light 15 and 17 is locally at or above a predetermined threshold, determination is made by the computer 27 that light 15 of a local quantity at or exceeding the threshold value has been emitted from an interior defect 16, and identification is made of the position of the interior defect 16 (position in the X direction and Y direction within the synthetic quartz glass substrate 4), and further of the type of interior defect 16 (regional striae, inclusions, foreign matter) from the shape and so forth of the light 15 of the local light quantity from the interior defect 16.

For example, in the event that there is regional striae or inclusions present in the synthetic quartz glass substrate 4 as a defect 16, introducing the ArF excimer laser light from the laser irradiation device 21 to the synthetic quartz glass substrate 4 causes the regional striae or inclusions to emit light 15 of a local quantity of the predetermined threshold (1000 counts) or more as illustrated in FIG. 3(A), while regions of the synthetic quartz glass substrate 4 other than the regional striae or the inclusions emit light 17. The computer 27 performs image processing analysis of the light 15 and 17 which the CCD camera 23 has received, thereby determining from the shape of the light 15 with the local quantity of the predetermined threshold or higher that the interior defect 16 is regional striae or inclusions, and detects the regional striae or inclusions along with the position thereof, judging that local striae or inclusions are present at the position where the light 15 of the regional quantity of the predetermined threshold or higher is situated. Now, in the case of FIG. 3(A), the horizontal axis represents the X directional position of the synthetic quartz glass substrate 4, and the vertical axis represents the quantity of light (intensity) of the light 15 and 17.

Also, in the event that there is foreign matter present in the synthetic quartz glass substrate 4 as a defect 16, introducing the ArF excimer laser light from the laser irradiation device 21 to the synthetic quartz glass substrate 4 causes the foreign matter to emit light 15 of a local quantity of the predetermined threshold (1000 counts) or more in a predetermined range D (e.g., 20 mm to 50 mm) as shown in FIG. 3(B), while regions of the synthetic quartz glass substrate 4 other than the regional striae or the inclusions emit light 17. The computer 27 performs image processing analysis of the light 15 and 17 which the CCD camera 23 has received, thereby determining from the shape of the light 15 with the local quantity of the predetermined threshold or higher that the interior defect 16 is foreign matter, and detects the foreign matter along with the position thereof, judging that local striae or inclusions are present at the position where the light 15 of the regional quantity of the predetermined threshold or higher is situated. Now, in the case of FIG. 3(B) as well, the horizontal axis represents the X directional position of the synthetic quartz glass substrate 4, and the vertical axis represents the quantity of light (intensity) of the light 15 and 17.

A synthetic quartz glass substrate 4, from which interior defects 16 are not detected by the defect detecting device 20 for the glass substrates, is subjected to precision polishing such that the principal surfaces 5 and 6 are a desired surface roughness, and subjected to cleansing processing, thereby obtaining a mask blank glass substrate 7 (FIG. 1(c)). The roughness of the principal surfaces 5 and 6 at this time is preferably 0.2 nm or less in root-mean-square roughness (RMS).

Now, regarding the above inspecting step, FIG. 4 illustrates the relation between the size of the ArF excimer laser light 25 and the end face 2 of the synthetic quartz glass substrate 4, as a preferable arrangement for introducing the ArF excimer laser light 25 from the laser irradiation device 21 to the end face 2 of the synthetic quartz glass substrate 4 as shown in FIG. 2. Also, at the time of introducing the ArF excimer laser light 25 from the laser irradiation device 21 to the end face 2 of the synthetic quartz glass substrate 4, causative substance which damages the surface of the synthetic quartz glass substrate 4 (particularly the principal surfaces 5 and 6) upon introduction of the ArF excimer laser light 25 is preferably eliminated from the ambient atmosphere.

That is to say, as shown in FIG. 5, the laser irradiation device 21, XYZ stage 22, and CCD camera 23, of the interior defect inspection device 20, and the synthetic quartz glass substrate 4 which is the subject to be inspected that is mounted on the XYZ state, are stored in the inner space A in a clean room 41. A filter room 42 having a fan 43 and a filter (chemical filter 44 using activated carbon for example) is formed at one side of the clean room 41.

The fan 43 is formed at the base of the filter room 42. Also, the chemical filter 44 is disposed at the generally center position in the vertical direction of a partition 45 sectioning the inner space A of the clean room 41 from the filter room 42. Air which has passed through the chemical filter 44 from the fan 43 passes through a facing wall 46 which is lattice-shaped for example, facing the partition 45, passes through an airflow path 47 formed on the bottom of the clean room 41, and is returned to the filter room 42 so as to be circulated. Passing the air through the chemical filter 44 removes causative substances such as chemical contaminants and the like which cause the above-described damage, so the inner space A of the clean room 41 is an atmosphere where clean air circulates.

The inner space A of the clean room 41 having the atmosphere wherein such clean air is circulated is an atmosphere with a cleanliness level higher than ISO class 5, preferably an atmosphere with a cleanliness level higher than ISO class 4, and further preferably an atmosphere with a cleanliness level higher than ISO class 3. Cleanliness as described here is a clean room standard stipulated in ISO 14644-1: 1999 (Cleanrooms and associated controlled environments—Part 1: Classification of air cleanliness).

Thus, chemical contaminants are removed from the inner space A of the clean room 41, so contaminants in the ambient atmosphere around the synthetic quartz glass substrate 4 loaded on the XYZ stage 22 become extremely rare, so adhesion or deposition of the contaminants on the surface of the synthetic quartz glass substrate 4, particularly on the principal surfaces 5 and 6 which have been polished to a mirror. Accordingly, trouble can be avoided wherein adhering matter and deposited matter which has adhered to the surface of the synthetic quartz glass substrate 4 (particularly on the principal surfaces 5 and 6 which have been polished to a mirror) absorbs the ArF excimer laser light 25 which is high-energy light and is heated, placing the surface of the synthetic quartz glass substrate 4 in a locally high-temperature state, thereby damaging the surface.

Also, the ArF excimer laser light 25 introduced to the end face 2 of the synthetic quartz glass substrate 4 from the laser irradiation device 21 in the inspection step has a beam shape which is greater than the width W of the end face 2 as shown in FIG. 4, and is perpendicularly introduced to the side face 51 of the end face 2.

That is to say, the end face 2 where the ArF excimer laser light 25 is introduced is configured having the side face 51 orthogonal to the principal surfaces 5 or 6 of the synthetic quartz glass substrate 4 where the thin film (later-described halftone film 8) to serve as a mask pattern is formed, and chamfered faces 52 and 53 between the side face 51 and the principal surfaces 5 and 6. The sum of the width W1 of the side face 51, the width W2 of the chamfered face 52, and the width W3 of the chamfered face 53, is the width W of the end face 2, and is, for example W=6.85 mm. Also, the ArF excimer laser light 25 introduced to this edge face 2 is ArF excimer laser light which has a quadrangle beam shape with a long side a×short side b (a=7.0 mm, b=4.0 mm), and power of 6 mJ (accordingly, energy (per pulse) per unit area is 21.4 mJ/cm$^2$), and frequency of 50 Hz.

Upon such ArF excimer laser light 25 being introduced from the laser irradiation device 21 to the end face 2 of the synthetic quartz glass substrate 4, the energy of the ArF excimer laser light 25 per unit area at the end face 2 is not too strong, so occurrence of plasma at the end face 2 is prevented. Moreover, the intensity of the light 15 generated at an interior defect 16 by the ArF excimer laser light 25 introduced to the end face 2 is sufficiently ensured to a detectable degree. Conditions for the ArF excimer laser light 25 necessary to prevent plasma from occurring as described above, while also sufficiently ensuring intensity of the light 15 is energy (per pulse) of 10 mJ/cm$^2$ or more but 50 mJ/cm$^2$ or less per unit area, and more preferably 15 mJ/cm$^2$ or more but 45 mJ/cm$^2$ or less. Also, the frequency is preferably 40 Hz or higher, in order to accurately detect interior defects 16 and improve inspection precision.

Also, the ArF excimer laser light 25 introduced to the edge face 2 has shape which is a quadrangle shape with a long side a×short side b (a=7.0 mm, b=4.0 mm), which is greater dimensions that the width W (6.85 mm) of the end face 2 of the synthetic quartz glass substrate 4 at the long side (a=7.0) side, so the ArF excimer laser light 25 is also irradiated in the plane direction of the principal surfaces 5 and 6 of the synthetic quartz glass substrate 4. Accordingly, even in the event that particles or contaminants 55 are adhering to the principal surfaces 5 and 6, these particles and contaminants 55 are blown off by the ArF excimer laser light 25 and can be removed. Note that while a quadrangle shape as been described for the shape of the ArF excimer laser light 25, circular or elliptical shapes having a diameter equal to or exceeding the width W of the end face 2 may be used.

Further, as long as there is no occurrence of plasma by the energy of the laser light within or around the synthetic quartz glass substrate 4, the ArF excimer laser light 25 may be parallel light, light with a certain expansion, or light converging with a certain level of angle. Parallel light, or light having a slight expansion is preferable. The expansion angle is preferably 6 mrad or less.

Note that with the above-described embodiment, introduction of the ArF excimer laser light to the synthetic quartz glass substrate 1 is performed with a state wherein the synthetic quartz glass substrate 4 is prepared by polishing the principal surfaces 5 and 6 which are the surface of the synthetic quartz glass substrate 1, and the opposing end faces 2 and 3, to a mirror, but the synthetic quartz glass substrate 4 may be in a state wherein only the end face 2 at the side where the ArF excimer laser light is to be introduced is polished to a mirror. Also, as with another embodiment shown in FIG. 6, the synthetic quartz glass substrate 4 may be in a state wherein the end face 2 and the end face 18 (FIG. 2) which is contiguous to the end face 2 and at which light generated by the interior defect 16 is received or sensed, are polished to a mirror. With the other embodiment shown in FIG. 6, in the stage of FIG. 6(*b*), the synthetic quartz glass substrate 4 is in a state wherein the end face 2 from which the ArF excimer laser light is introduced, and the end face 18 which is contiguous to the end face 2 and at which light generated by the interior defect 16 is received or sensed, are polished to a mirror to a degree wherein the ArF excimer laser light can be introduced, and light generated by the interior defect 16 can be received or sensed. In FIG. 6, the stages other than FIG. 6(*b*) are performed in the same way as with FIG. 1.

That is to say, in the preparation step of the synthetic quartz glass substrate, an arrangement may be made wherein, of the surfaces of the synthetic quartz glass substrate 4, the remaining end face 19 (FIG. 2) and the opposing principal surfaces 5 and 6 are not polished to a mirror had have a surface roughness of around 0.5 μm, but the aforementioned end faces 2 and 18 have a surface roughness of around 0.03 μm or less.

As described above, optical inhomogeneity of the synthetic quartz glass substrate 4, i.e., interior defects 16 leading to transfer pattern defects, are sensed or detected at an early stage (the stage of FIG. 6(*b*)) prior to precision polishing of the principal surfaces of the synthetic quartz glass substrate 4 in the mask blank glass substrate manufacturing process, meaning that precision polishing is performed for the principal surfaces and other end faces only for synthetic quartz glass substrate 4 in which there is no optical inhomogeneity upon introduction of the ArF excimer laser to the synthetic quartz glass substrate 4, so waste in the manufacturing process of the glass substrate for a mask blank can be cut down on.

In the event of performing the inspection step using the ArF excimer laser light in a state wherein the principal surface of the synthetic quartz glass substrate 4 has not been mirror polished, there is the need to sense or detect regional or local optical inhomogeneities from the end face 18 of the synthetic quartz glass substrate 4, so the inspection step is performed with a defect inspecting device such as shown in FIG. 7. Note that in FIG. 7, components with the same configuration as in FIG. 2 will be described having been denoted with the same reference numerals.

The defect inspecting device shown in FIG. 7 includes a laser irradiation device 21 serving as light introducing means for introducing ArF excimer laser light which is light of the exposure wavelength (i.e., light of the same wavelength as the exposure wavelength) from the end face 2 of the synthetic quartz glass substrate 4, and XYZ stage 22 upon which the synthetic quartz glass substrate 4 is placed in moved in the X direction, Y direction, and Z direction, as to the laser light emitted from the laser irradiation device 21, and a CCD device and a lens for widening the detection range of the CCD device (both unshown) disposed on the end face 33 side of the synthetic quartz glass substrate 4 placed on the XYZ stage 22, and has a CCD camera (line sensor camera) 23 serving as photoreceptor means having a detection field 24 over the entire range of the width direction of the synthetic quartz glass substrate 4 (i.e., the irradiation direction of the laser light irradiated from the laser irradiation device 21), and a computer 27 serving as detecting means, connected to the CCD camera 23 using a USB cable 26.

The laser irradiation device 21 sequentially introduces the ArF excimer laser light from each position in the Y direction at the end face 2 of the synthetic quartz glass substrate 4 (i.e., the longitudinal direction of the end face 2), while the XYZ stage 22 moves the synthetic quartz glass substrate 4 in the Y direction. Accordingly, the ArF excimer laser light 25 is scanned in the longitudinal direction (the α direction in FIG. 4(A)) of the end face 2 of the synthetic quartz glass substrate 4. Also, the CCD camera 23 receives and captures light from the end face 18 side of the synthetic quartz glass substrate 4 for each position in the Y direction of the synthetic quartz glass substrate 4, regarding the light 15 and 17 having a wavelength longer than the wavelength λ1, which the synthetic quartz glass substrate 4 emits due to the ArF excimer laser light (wavelength of λ1) being irradiated into each position in the Y direction at the end face 2 of the synthetic quartz glass substrate 4.

Also, in the above embodiment, an example has been described wherein the ArF excimer laser light 25 from the laser irradiation device 21 is perpendicularly introduced to a side face perpendicular to the principal surfaces 5 and 6 at the end face of the synthetic quartz glass substrate 4. However, an arrangement may be made wherein, following prediction polishing of the principal surfaces 5 and 6 and the side faces (e.g., side faces of the end faces 2 and 3) of the synthetic quartz glass substrate 4, ArF excimer laser light 25 is introduced into the synthetic quartz glass substrate 4 under the condition that the light is introduced from one of the chamfered faces formed between the side faces and principal surfaces 5 and 6 to effect total reflection at the principal surfaces 5 and 6 and the side faces. In this case, the ArF excimer laser light 25 becomes essentially trapped within the synthetic quartz glass substrate 4, but in the event that an adhering matter or the like is adhering to the surface of the synthetic quartz glass substrate 4, the condition of total reflection does not hold, so the ArF excimer laser light 25 leaks out, and the leaked ArF excimer laser light 25 is absorbed by the adhering matter and makes a regionally or locally high-temperature state on the surface of the synthetic quartz glass substrate 4, thereby damaging the synthetic quartz glass substrate 4. In this case, in the event that the synthetic quartz glass substrate 4 is on the clean atmosphere within the inner space A of the clean room 44 as shown in FIG. 5, no adhering matter adheres to the surface of the synthetic quartz glass substrate 4, and accordingly, occurrence of damage can be prevented. Or, an arrangement may be made wherein, following precision polishing of the principal surfaces 5 and 6 of the synthetic quartz glass substrate 4, the ArF excimer laser light 25 is introduced from the principal surfaces 5 and 6.

Also, regarding introducing the ArF excimer laser light from the end face 2 of the synthetic quartz glass substrate 4 in the above embodiment, the four corners of the synthetic quartz glass substrate 4 which is the mask blank glass substrate are round chamfered (rounded), so upon ArF excimer laser light being irradiated to the four corners that have been round chamfered, the lens effects of the rounded faces collect light in the synthetic quartz glass substrate 4, is the energy of the ArF excimer laser light that has been introduced becomes high, and there are cases of damage occurring at the focal point. Depending on the focal point, damage inside the substrate causes change in optical properties as to the exposure light (e.g., drop of transmissivity), leading to transfer pattern defects, which is undesirable. Also, collecting the ArF excimer laser light with the rounded faces can lead to cracking of the substrate in the event that internal damage to the substrate is great, which is undesirable. In this case, shielding means (not shown) are preferably used to shield such that there is no irradiation of the ArF excimer laser light on the four corners of the synthetic quartz glass substrate. Thus, internal damage to the substrate by the ArF excimer laser light by lens effects of the rounded faces can be prevented.

Also, while ArF excimer laser, which is the same as the inspection light and the exposure light, has been used in the above embodiment, this does not necessarily have to be the same as the inspection light and exposure light, and may be laser light having a wavelength of 200 nm or shorter, or a light source with a wavelength of 200 nm or shorter. Preferable is light having a wavelength of 200 nm or shorter with transmissivity of 80% or higher with regard to the synthetic quartz glass substrate which is the mask blank glass substrate, and more preferably 85% or higher. Preferably, light with a wavelength of the 100 nm to 200 nm will suffice, and F2 excimer laser may be used. Or, an arrangement may be made wherein, in order to obtain light with the same wavelength as the ArF excimer laser or F2 excimer laser, light from a light source such as a deuterium (D2) lamp or the like, is subjected to spectroscopy and the central wavelength having the same wavelength as ArF excimer laser or F2 excimer laser is used. However, using the same light for the inspection light and exposure light is preferably, since optical inhomogeneities inspection can be performed under the actual pattern transfer environment.

Also, while the above embodiment has been described using photoreceptor means to detect optical inhomogeneities, in the event that there is no need to identify the type of optical inhomogeneity, i.e., the type of interior defect 16 which would become a transfer pattern defect, the inspection step may be carried out by visual sensing of light (fluorescence) regionally or locally emitted, in a state wherein protection is in place using a transparent acrylic material capable of cutting out ultraviolet wavelengths which affect the human body. Also, while light 15 and 17 having a wavelength longer than the exposure wavelength light (inspection light), emitted by interior defects 16 in the synthetic quartz glass substrate 4 and regions other than the interior defects 16, have been described as being received with the CCD camera 23, but an arrangement may be made wherein the inspection step is performed by a spectroscope receiving the light 15 and 17 and measuring the spectral properties (wavelength and intensity) of the interior defect 16 and intensity (quantity of light) of the light 15 and 17, thereby sensing or detecting the interior defect 16. Also, an arrangement may be made wherein the inspection step is performed by a color camera being used for the CCD camera 23, and light 15 and 17 having a wavelength longer than the exposure wavelength light (inspection light), emitted by interior defects 16 in the synthetic quartz glass substrate 4 and regions other than the interior defects 16, is received and captured, the images of the CCD camera 23 are subjected to image processing by color such as red, green, blue, and so forth, by the computer 27, and the interior defects 16 are sensed or detected based on information such as the intensity (quantity of light) distribution of the light subjected to image processing by color or information regarding wavelength of the light or the like. Further, detection of interior defects 16 may be performed at the final stage in the manufacturing process of the mask blank glass substrates.

Also, with above embodiment, an example has been described wherein, at the time of introducing the ArF excimer laser light to the synthetic quartz glass substrate 4, light regionally or locally emitted by the interior defect 16, and light emitted by regions other than the interior defect 16 are sensed or detected, but the present invention is not restricted to this arrangement, and the inspection step may performed with an arrangement wherein regions other than the interior defect 16 do not emit light even upon introducing the ArF excimer laser light into the synthetic quartz glass substrate 4, so only light regionally or locally emitted from the interior defect 16 alone is sensed or detected.

Also, while the above embodiment described a synthetic quartz glass substrate used as the transparent substrate for a mask blank, in the case of using ArF excimer laser as the exposure light, but the present invention is not restricted to this, an transparent quartz glass obtained by melting a quartz ingredient may be used. Also, in the event that the exposure light is F2 excimer laser, a calcium fluoride (CaF2) substrate or a glass substrate doped with fluorine may be used.

Also, while the above embodiment has described transparent substrates for mask blanks to be the subject of inspection, the present invention is not restricted to this, and in the case of the state before forming a transparent substrate for a mask blank, or a synthetic quartz glass substrate, inspection may be performed on articles in the state of synthetic quartz glass ingot in which synthetic quartz glass is generated, the state of blocks cut out from the synthetic quartz glass ingot, or the state of plates cut our from the blocks. Also, optical components used in an exposure device used for photolithography such as lenses, or articles in the state before being worked into lenses, may be the subject of inspection.

[B] Manufacturing Method for Mask Blank

Next, a thin film (halftone film 8) to serve as a mask pattern is formed by sputtering on the principal surface 5 of a mask blank glass substrate 7, and a mask blank 9 (halftone-type phase-shift mask blank) is fabricated (FIG. 1(d)). Film formation of the halftone film 8 is performed using a sputtering device having the following configuration, for example.

The sputtering device is a DC magnetron sputtering device 30 such as shown in FIG. 8, having a vacuum chamber 31 with a magnetron cathode 32 and substrate holder 33 within the vacuum chamber 31. A sputtering target 35 adhered to a backing plate 34 is mounted to the magnetron cathode 32. For example, oxygen-free copper is used for the baking plate, and indium is used for adhering the sputtering target 35 and the backing plate 34. The backing plate 34 is either directly or indirectly cooled by a water-cooling mechanism. Also, the magnetron cathode 32, baking plate 34, and sputtering target 35 are electrically joined. A glass substrate 7 is mounted to the substrate holder 33.

As shown in FIG. 9, the sputtering target 35 and the glass substrate 7 are disposed such that the opposing faces of the glass substrate 7 and the sputtering target 35 assume a predetermined angle (target inclination angle) θ. Thus, a thin film (halftone film 8) to serve as a mask pattern is uniformly formed on the principal surface of the glass substrate 7, so irregularities in transmissivity within the substrate face to serve as the mask blank can be suppressed. In this case, the offset distance d between the sputtering target 35 (the target center thereof) and the glass substrate 7 (the substrate center thereof) is 340 mm, and the perpendicular distance (T/S) between the sputtering target 35 and the glass substrate 7 is 380 mm, and the inclination angle of the sputtering target is 15°.

The vacuum chamber 31 shown in FIG. 8 is drawn using a vacuum pump from an exhaust opening 37. Following the atmosphere within the vacuum chamber 31 reaching a degree of vacuum to where there is no affect on properties of the film to be formed, a gas mixture including nitrogen is introduced from a gas inlet 38, and negative voltage is applied to the magnetron cathode 32 using a DC power source 39, thereby performing sputtering. The DC power source 39 has arc detecting functions, and monitors the discharge state during sputtering. The internal pressure of the vacuum chamber 31 is measured by a pressure gauge 36.

[C] Manufacturing Method for Exposure Mask

Next, as shown in FIG. 1, following applying a resist on the surface of the halftone film 8 of the mask blank 9 (halftone-type phase-shift mask blank), heating processing is performed to form a resist film 10 (FIG. 1(e)).

Next, a predetermined pattern is drawn on the resist film 10 on the mask blank 11 with the resist film, and developed, thereby forming a resist pattern 12 (FIG. 1(f)).

Next, using the resist pattern 12 as a mask, the halftone film 8 is subjected to dry etching, thereby forming a halftone film pattern 13 as a mask pattern (FIG. 1(g)).

Finally, the resist pattern 12 is removed, thereby obtaining an exposure mask 14 wherein the halftone film pattern 13 is formed on the glass substrate 7 (FIG. 1(h)).

Note that while with the above embodiment, description has been made with regard to halftone-type phase-shift mask blanks wherein halftone film is formed on a glass substrate for a mask blank, and halftone-type phase-shift masks wherein halftone film patterns are formed on glass substrates for mask blanks, but the present invention is not restricted to these. For example, a halftone-type phase-shift mask blank wherein a halftone film is formed on a mask blank glass substrate 7 and an opaque film is formed on the halftone film may be formed. Also, this may be a halftone-type phase-shift mask wherein an opaque film pattern is formed for increasing shielding functions at desired positions on the halftone film pattern, used as a halftone-type phase-shift mask obtained from this halftone-type phase-shift mask blank.

Also, this may be a photo-mask blank wherein an opaque film is formed on the mask blank glass substrate 7, or a blank for chromium-free use, wherein a thin film for forming a mask pattern for fabricating a chromium-free mask is formed by forming a lowered and raised pattern by engraving the surface of a mask blank glass substrate by etching to a desired depth.

Note that in the event that optical inhomogeneities exist in a transparent substrate for a mask blank, the advantages of the present invention are more clearly manifested with an inspection method of a transparent substrate for a phase-shift mask blank where effects of the transfer pattern due to change in optical properties with regard to exposure light, and the manufacturing method for a transparent substrate for a phase-shift mask blank. Most particularly, the advantages of the present invention are further clearly manifested with an inspection method of a transparent substrate and manufacturing method of a transparent substrate for a phase shift mask wherein the transmissivity of the mask pattern of an exposure mask with regard to the exposure light is 10% or more (e.g., a tri-tone type phase-shift mask wherein a halftone film having 10% or higher transmissivity with regard to the exposure light and an opaque film have been formed, or a chromium-less type phase-shift mask).

Note that the phase-shift mask blank such as these halftone-type phase-shift mask blanks or chromium-less mask blanks, and photomask blanks, may be mask blanks with resist, wherein a thin film for forming a mask pattern has been formed and a resist film has been formed on the thin film for forming a mask pattern.

[D] Manufacturing Method for Semiconductor Device

The obtained exposure mask 14 is mounted in an exposure device, the exposure mask 14 is used to transfer the mask pattern of the exposure mask onto a resist film formed on a semiconductor substrate (semiconductor wafer) using photolithography with ArF excimer laser as the exposure light, so as to form a desired circuit pattern on the semiconductor substrate, thereby manufacturing a semiconductor device.

[E] Advantages

Due to the above configuration, the above-described embodiment has the following advantages.

(1) With a defect inspecting device 20 of transparent articles such as glass articles, ArF excimer laser light which is an inspection light having a wavelength of 200 nm or shorter (and which also is the exposure light wavelength) is introduced by a laser irradiation device 21 which is light introducing means, from a surface (end face 2) of a synthetic quartz glass substrate 4 which is a transparent article, light 15 having a wavelength longer than the above wavelength emitted from an interior defect 16 within the synthetic quartz glass substrate 4 and light 17 having a wavelength longer than the above wavelength emitted from regions within the synthetic quartz glass substrate 4 other than the interior defect 16 are received by a CCD camera 23 which is photoreceptor means from a principal surface of the synthetic quartz glass substrate 4 or an end face 33 which is different from the end face 2, a computer 27 which is detecting means subjects the received light 15 and 17 to image processing, and detects interior defects 16 within the synthetic quartz glass substrate 4 based on difference in quantity of light between the light 15 and light 17. Using light having a wavelength of 200 nm or shorter for inspection of interior defects 16 of the synthetic quartz glass substrate 4 which is a transparent article used in photolithography in this way allows the interior defects 16 to be detected well.

(2) ArF excimer laser light which is an inspection light having a wavelength of 200 nm or shorter (and which also is the exposure light wavelength) is introduced from the end face 2 of a synthetic quartz glass substrate 4 which is a transparent substrate for a mask blank, light 15 having a wavelength longer than the above wavelength emitted from an interior defect 16 which is a regional optical inhomogeneity of the synthetic quartz glass substrate 4 and light 17 having a wavelength longer than the above wavelength emitted from regions within the synthetic quartz glass substrate 4 other than the interior defect 16, are received from a principal surface of the synthetic quartz glass substrate 4 or an end face 33 which is different from the end face 2, interior defects 16 are detected based on difference in quantity of light between the received light 15 and light 17, and mask blank glass substrates 7 are manufactured using synthetic quartz glass substrates 4 from which no interior defects 16 have been detected. Consequently, there are no interior defects 16 in glass substrates 7 of exposure masks 14 manufactured from the mask blank glass substrates 7 via mask blanks 9. Accordingly, there are no regions in the exposure masks 14 where optical properties locally change (e.g., drop of transmissivity) due to interior defects 16 of the glass substrate 7, so excellent transfer precision can be had without adverse affects on pattern transfer causing transfer pattern defects.

(3) The defect inspecting device 20 is used to detect interior defects 16 in the synthetic quartz glass substrates 4 at an early stage in the manufacturing process of the mask blank glass substrate which is a transparent substrate 7 for a mask blank, prior to precision polishing of the principal surfaces 5 and 6, so the principal surfaces 5 and 6 are subjected to precision polishing only for synthetic quartz glass substrates 4 with no interior defects 16, and the waste of precision polishing of the principal surfaces 5 and 6 of synthetic quartz glass substrates 4 with interior defects 16 can be cut out.

(4) ArF excimer laser light which is an inspection light having a wavelength of 200 nm or shorter (and which also is the exposure light wavelength) is introduced to a synthetic quartz glass substrate 4 which is a transparent substrate for a mask blank, and inspection for interior defects 16 of the glass substrate is performed. Accordingly, interior defects 16 which would be transfer pattern defects at the time of pattern transfer using the exposure mask 14, manufactured from the synthetic quartz glass substrate 4 via the mask blank glass substrate 7 and mask blank 9, and the exposure light, can be detected well. The synthetic quartz glass substrates 4 from which no interior defects 16 are detected and wherein there is no damage on the principal surfaces 5 and 6 are used to manufacture the mask blank glass substrate 7, so there are no regions in the exposure masks 14 using the mask blank glass substrates 7 wherein optical properties regionally or locally change (e.g., drop of transmissivity) due to interior defects 16 in the glass substrate or damage to the principal surfaces 5 and 6, so no transfer pattern defects occur, and transfer precision can be improved.

(5) In the interior defect 16 detecting step, the synthetic quartz glass substrate 4 which is the inspection subject, has been placed in the internal space A of a clean room 41 through which clean air circulates, so at the time of introducing the ArF excimer laser light 25 which is inspection light, into the synthetic quartz glass substrate 4, the ArF excimer laser light 25 can be introduced to the synthetic quartz glass substrate 4 in the state wherein causative substance which causes damage to the surface (particularly principal surfaces 5 and 6) of the glass substrate 4 at the time of introducing the ArF excimer laser light 25 has been eliminated from the ambient atmosphere of the synthetic quartz glass substrate 4. Consequently, damage to the surface due to adhering matter and deposited matter adhering to the surfaces (particularly the principal surfaces 5 and 6) of the synthetic quartz glass substrate 4 absorbing the ArF excimer laser light 25 and making the temperature of the surface regionally or locally high, can be prevented.

(6) The beam shape (quadrangle shape, long side a×sort side b) of the ArF excimer laser light 25 introduced to the end face 2 of the synthetic quartz glass substrate 4 which is a transparent substrate for a mask blank, has been set larger than the width W of the end face 2 from which the ArF excimer laser light 25 is introduced, so the energy (per pulse) of the laser light 25 per unit area at the end face 2 is not too strong, so occurrence of plasma at the end face 2 can be avoided. Consequently, a situation wherein contamination or foreign matter adhering to the end face 2 damages the end face 2 by plasma can be prevented, and detection procession of interior defects 16 can be improved.

(7) The energy (per pulse) per unit area of the ArF excimer laser light 25 introduced to the end face 2 of the synthetic quartz glass substrate 4 which is a transparent substrate for a mask blank is 10 mJ/cm$^2$ or more but 50 mJ/cm$^2$ or less, so occurrence of plasma at the end face 2 due to the ArF excimer laser light 25 can be avoided, and also the intensity of the light 15 and 17 generated at interior defects 16 within the synthetic quartz glass substrate 4 due to introduction of the ArF excimer laser light 25 is sufficiently ensured, and accordingly reliability of defect detection precision can be maintained.

(8) The of the ArF excimer laser light 25 introduced to the end face 2 of the synthetic quartz glass substrate 4 which is a transparent substrate for a mask blank has a beam shape (quadrangle shape, long side a×sort side b) larger than the width W of the end face 2, and further the ArF excimer laser light 25 is scanned in the longitudinal direction (the α direction in FIG. 4(A)) of the end face 2 of the synthetic quartz glass substrate 4, so the ArF excimer laser light 25 is irradiated on both principal surfaces 5 and 6 contiguous to the end face 2. Accordingly, particles and contaminants 55 adhering to both principal surfaces 5 and 6 can be removed by the ArF excimer laser light 25.

First Embodiment

A synthetic quartz glass substrate obtained by being cut out to a size of 152.4 mm×152.4 mm×6.85 mm from synthetic quartz glass base material (synthetic quartz glass ingot) generated with silicon tetrachloride and so forth as the starting material was shaped and chamfered, whereby ten synthetic quartz glass substrates having surface roughness of the end face where ArF excimer laser light (wavelength: 193 nm) which is the inspection light is to be introduced (the side orthogonal to the principal surface where the thin film is formed, and chamfered face formed between the principal surface and the side face) of a maximum height Rmax of 0.5 µm or less, were obtained. Note that the principal surfaces of the synthetic quartz glass substrates have not yet been subjected to mirror polishing or precision polishing, and according are in a frosted-glass state.

Next, the defect inspecting device described in the above embodiment was used to introduce ArF excimer laser light with a beam shape of 7.0 mm×4.0 mm which is larger than the thickness of the synthetic quartz glass substrate, energy per pulse of 6 mJ, and frequency of 50 Hz, to the end face of the synthetic quartz glass substrate, and inspection of inner defects was performed.

Observation of interior defects of the synthetic quartz glass substrate were performed by visually observing from another end face which differs from the end face from which the ArF excimer laser light was introduced, and which is orthogonal to the optical path of the ArF excimer laser light.

As a result of interior defect inspection of the synthetic quartz glass substrates, four of the ten exhibited regionally or locally shining inhomogeneous regions, in dot shapes, elliptical shapes, or cracked-stratum shapes. The dot-shaped light was confirmed as light-bluish fluorescence, the elliptically shaped light as light-bluish fluorescence and yellowish fluorescence, and the cracked-stratum shaped light as yellowish fluorescence.

The synthetic quartz glass substrates regarding which regionally or locally shining inhomogeneous regions were not confirmed were subjected to precision polishing of the principal surfaces and end faces (side faces and chamfered faces), thereby obtaining glass substrates for mask blanks.

The physical properties of the obtained glass substrates for mask blanks were measured with a transmissivity measurement system at nine positions in the thickness direction in the mask pattern formation region (132 mm×132 mm) of the glass substrates, for transmissivity of a wavelength of 193 nm. The difference between maximum transmissivity and minimum transmissivity was within 2% (i.e., optical loss of the glass substrates was within 3%/cm), which is excellent. Note that measurement of transmissivity was performed by irradiating measurement light of a deuterium lamp (wavelength of 193 nm) and calculating from the difference between incident light quantity and output light quantity of the inspection light.

The glass substrates for mask blanks were used to fabricate three each of a high-transmissivity halftone-type phase-shift mask blank formed by sequentially forming a halftone film having transmissivity of 20% as to ArF excimer laser light and phase difference of 180°, an opaque film with optical concentration of 3 or higher, and a resist film, and a photo-mask blank formed by sequentially forming a shield film with optical concentration of 3 or higher as to ArF excimer laser light, and a resist film.

A halftone-type phase-shift mask was fabricated from the halftone-type phase-shift mask blank, and a photomask from the photomask blank.

The fabricated halftone-type phase-shift mask and photomask were each mounted to an exposure device (stepper) using ArF excimer laser (wavelength of 193 nm) as the exposure light source, and circuit patterns were formed on a semiconductor substrate, thereby fabricating semiconductor devices.

The obtained semiconductor devices had no circuit pattern defects and were all satisfactory.

As described above, synthetic quartz glass substrates with no interior defects, where transmissivity deteriorates, present in the synthetic quartz glass substrates, can be selected at the stage prior to precision polishing of the principal surface in the manufacturing process of glass substrates for mask blanks, and precision polishing can be performed only for the principal surfaces of the selected synthetic quartz glass substrates to manufacture glass substrates for mask blanks. Accordingly, with the inspection method according to the present invention, precision polishing of synthetic quartz glass substrates with interior defects can be avoided, so waste can be cut out.

Comparative Embodiment

On the other hand, in order to make a comparison with the above embodiment, a halftone-type phase-shift mask blank and a photomask blank were fabricated using synthetic quartz glass substrates in which fluorescence, where light is locally emitted, had been confirmed in the above inspection step, in the same way as described above, following which a halftone-type phase-shift mask and a photomask were respectively fabricated. Circuit patterns were formed on a semiconductor substrate by photolithography in the same way as above using the fabricated halftone-type phase-shift mask and photomask, which resulted in pattern defects such as circuit patterns not being formed.

The above photomask was evaluated regarding transfer properties, using a Microlithography Simulation Microscope AIMS 193 (manufactured by Carl Zeiss), wherein was confirmed drop of transmissivity of approximately 5% to approximately 40% in regions (in the order to tens of µm to hundreds of µm) which had been locally emitting light as fluorescence.

Second Embodiment

The inspection of synthetic quartz glass substrates was performed in the same way with the above first embodiment, other than interior defects of the synthetic quartz glass substrates being inspected using a defect detecting device placed in an atmosphere where clean air circulates (ISO class 4, using chemical filter), and further, precision polishing of the principal surfaces was performed, thereby obtaining glass substrates for mask blanks. Consequently, inspection of interior defects of the synthetic quartz glass substrates was performed without any damage to the end face from which the ArF excimer laser light is introduced, and synthetic quartz glass substrates in which local fluorescence light is not emitted were selected. The principal surfaces of the selected synthetic quartz glass substrates were subjected to precision polishing and glass substrates for mask blanks were manufactured, and further, a halftone-type phase-shift mask blank and a photomask blank were fabricated, with which semiconductor devices were fabricated by photolithography, with no circuit pattern defects occurring.

Third Embodiment

An introduction face for introducing ArF excimer laser light was formed on synthetic quartz glass base material (synthetic quartz glass ingot) generated with silicon tetrachloride and so forth as the starting material, and ArF excimer laser light was introduced from the introduction face to inspect the interior of the synthetic quartz glass base material for inner defects. Note that the introduction face was formed by locally mirror polishing the surface of the synthetic quartz glass base material so as to obtain a mirror face of a size larger than the beam shape of the ArF excimer laser light.

Regions not locally emitting fluorescence at the time of introducing the ArF excimer laser light to the synthetic quartz glass base material were identified, and synthetic quartz glass blocks were cut out only from the identified regions, from which lenses for an exposure device (stepper) using the ArF excimer laser as the exposure light source, and glass substrates for mask blanks, were fabricated.

The obtained lenses and glass substrates for mask blanks were evaluated regarding any drop of transmissivity of the ArF excimer laser light. The articles were excellent with almost not drop of transmissivity at all, such that there is no problem in use as lenses for an exposure device (stepper) and glass substrates for mask blanks.

Fourth Embodiment

Photomasks and further semiconductor devices were fabricated in the same way as with the first embodiment, except for fabricating a photomask blank by sequentially forming an opaque film with optical concentration of 3 or higher as to ArF excimer laser light, and a resist film, on a glass substrate of which the transmissivity in the thickness direction of a synthetic quartz glass substrate, selected in the above-described inspection step in the above first embodiment, was within 5% for the difference between maximum transmissivity and minimum transmissivity (i.e., optical loss of the glass substrate of 8%/cm or less). The semiconductor devices obtained as a result were all excellent with no circuit pattern defects.

Referential Example

Interior defects of synthetic quartz glass substrates were inspected for in the same way as with the second embodiment, except for performing inspection of interior defects of the synthetic quartz glass substrate in the second embodiment using a defect inspection device placed in the atmosphere with no cleanliness management.

As a result, plasma occurred around the end face during irradiation of the ArF excimer laser light at the end face of the synthetic quartz glass substrate, and damaged the end face of the synthetic quartz glass substrate. Such damage is undesirable since it leads to dusting, which in turn causes mask pattern defects, in the mask blank manufacturing processes, or at the time of storing the mask blanks in storage containers, or at the time of transporting mask blanks, in the event that precision polishing of the end face is not performed in the subsequent mask blank manufacturing processing, or in cases wherein precision polishing of the end face is performed but damage is deep and the working margin for precision polishing of the end face is small. Note that in the event that damage is not deep and the working margin for precision polishing of the end face is greater, this does not lead to the above dusting and is not problematic.

The invention claimed is:

1. A transparent substrate for a mask blank, comprising said transparent substrate configured such that, upon introduction of light having a wavelength of 200 nm or shorter from one side of a surface of said transparent substrate, the loss of light having a wavelength longer than said wavelength that is generated regionally or locally within said transparent substrate is 8%/cm or lower within a mask pattern formation region of said transparent substrate.

2. The transparent substrate for a mask blank according to claim 1, wherein said transparent substrate for a mask blank is a transparent substrate for a phase-shift mask blank.

3. The transparent substrate for a mask blank according to claim 2, wherein the loss of light having a wavelength longer than said wavelength that is generated regionally or locally within said transparent substrate is 3%/cm or lower within the mask pattern formation region of said transparent substrate.

4. The transparent substrate for a mask blank according to claim 1, wherein said transparent substrate for a mask blank is formed of synthetic quartz glass.

5. A mask blank comprising: a transparent substrate, said transparent substrate configured such that, upon introduction of light having a wavelength of 200 nm or shorter from one side of a surface of said transparent substrate, the loss of light having a wavelength longer than said wavelength that is generated regionally or locally within said transparent substrate is 8%/cm or lower within a mask pattern formation region of said transparent substrate; and a thin film to serve as a mask pattern, or a thin film for forming a mask pattern, formed on a principal surface of said transparent substrate.

6. The mask blank according to claim 5, wherein said mask blank is a phase-shift mask blank, and wherein the loss of light having a wavelength longer than said wavelength that is generated regionally or locally within said transparent substrate is 3%/cm or lower within the mask pattern formation region of said transparent substrate.

7. The mask blank according to claim 5, wherein said mask blank is a phase-shift mask blank, and wherein transmissivity of the thin film with regard to an exposure light is 10% or more.

8. The mask blank according to claim 5, further comprising a resist film formed on the thin film.

9. An exposure mask comprising: a transparent substrate, said transparent substrate configured such that, upon introduction of light having a wavelength of 200 nm or shorter from one side of a surface of said transparent substrate, the loss of light having a wavelength longer than said wavelength that is generated regionally or locally within said transparent substrate is 8%/cm or lower within a mask pattern formation region of said transparent substrate; and a mask pattern of a thin film pattern formed on a principal surface of said transparent substrate.

10. The exposure mask according to claim 9, wherein said exposure mask is a phase-shift mask, and wherein transmissivity of the mask pattern with regard to an exposure light is 10% or more.

11. An exposure mask comprising: a transparent substrate, said transparent substrate configured such that, upon introduction of light having a wavelength of 200 nm or shorter from one side of a surface of said transparent substrate, the loss of light having a wavelength longer than said wavelength that is generated regionally or locally within said transparent substrate is 8%/cm or lower within a mask pattern formation region of said transparent substrate; and a mask pattern formed on a principal surface of said transparent substrate by etching said transparent substrate.

12. The exposure mask according to claim 11, wherein said exposure mask is a phase-shift mask, and wherein transmissivity of the mask pattern with regard to an exposure light is 10% or more.

13. A phase shift mask blank for use in manufacturing a phase shift mask that is exposed to an exposure light not longer than a wavelength of 200 nm, comprising: a transparent substrate; and a semi-transparent film on a principal surface of the transparent substrate; wherein said transparent substrate is configured such that an interior defect of the transparent substrate is not detected, the interior defect causing a transfer pattern defect and emitting fluorescence when inspection light having the same wavelength as the exposure light is introduced into the transparent substrate; and wherein the semi-transparent film has a transmissivity which is not less than 10% for the exposure light.

14. The phase shift mask blank according to claim 13, wherein upon introduction of light having a wavelength of 200 nm or shorter from the principal surface of said transparent substrate, the loss of the fluorescence is 3%/cm or lower within a mask pattern formation region of said transparent substrate.

15. The phase shift mask blank according to claim 13, further comprising an opaque film on the semi-transparent film.

16. The phase shift mask blank according to claim 15, further comprising a resist film on the opaque film.

17. A phase shift mask that is exposed to an exposure light not longer than a wavelength of 200 nm, comprising: a transparent substrate; and a mask pattern of a thin film pattern formed on a principal surface of said transparent substrate; wherein said transparent substrate is configured such that an interior defect of the transparent substrate is not detected, the interior defect causing a transfer pattern defect and emitting fluorescence when inspection light having the same wavelength as the exposure light is introduced into the transparent substrate; and wherein the mask pattern has a transmissivity which is not less than 10% for the exposure light.

18. The phase shift mask according to claim 17, wherein upon introduction of light having a wavelength of 200 nm or shorter from the principal surface of said transparent substrate, the loss of the fluorescence is 3%/cm or lower within a mask pattern formation region of said transparent substrate.

19. A phase shift mask that is exposed to an exposure light not longer than a wavelength of 200 nm, comprising: a transparent substrate; and a mask pattern formed on a principal surface of said transparent substrate by etching said transparent substrate; wherein said transparent substrate is configured such that an interior defect of the transparent substrate is not detected, the interior defect causing a transfer pattern defect and emitting fluorescence when inspection light having the same wavelength as the exposure light is introduced into the transparent substrate; and wherein the mask pattern has a transmissivity which is not less than 10% for the exposure light.

20. The phase shift mask according to claim 19, wherein upon introduction of light having a wavelength of 200 nm or shorter from the principal surface of said transparent substrate, the loss of the fluorescence is 3%/cm or lower within a mask pattern formation region of said transparent substrate.

* * * * *